(12) United States Patent
Wang et al.

(10) Patent No.: US 8,465,917 B2
(45) Date of Patent: Jun. 18, 2013

(54) METHODS FOR DETERMINING HEPTOCELLULAR CARCINOMA SUBTYPE AND DETECTING HEPATIC CANCER STEM CELLS

(75) Inventors: Xin Wei Wang, Rockville, MD (US); Junfang Ji, Clarksburg, VA (US); Taro Yamashita, Ishikawa (JP); Carlo M. Croce, Columbus, OH (US)

(73) Assignees: The Ohio State University Research Foundation, Columbus, OH (US); The United States of America, as represented by the Secretary of the Department of Health and Human Services, National Institutes of Health, Office of Technology Transfer, Washington, DC (US)

( * ) Notice: Subject to any disclaimer, the term of this patent is extended or adjusted under 35 U.S.C. 154(b) by 450 days.

(21) Appl. No.: 12/663,586

(22) PCT Filed: Jun. 9, 2008

(86) PCT No.: PCT/US2008/007196
§ 371 (c)(1),
(2), (4) Date: Apr. 21, 2010

(87) PCT Pub. No.: WO2008/153987
PCT Pub. Date: Dec. 18, 2008

(65) Prior Publication Data
US 2010/0197770 A1    Aug. 5, 2010

Related U.S. Application Data

(60) Provisional application No. 60/942,833, filed on Jun. 8, 2007.

(51) Int. Cl.
*C12Q 1/68* (2006.01)

(52) U.S. Cl.
USPC ......................................................... 435/6.1

(58) Field of Classification Search
None
See application file for complete search history.

(56) References Cited

U.S. PATENT DOCUMENTS

| | | | |
|---|---|---|---|
| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,585,969 B2 | 9/2009 | Stoffel et al. |

(Continued)

FOREIGN PATENT DOCUMENTS

| | | |
|---|---|---|
| CA | 2587189 | 12/2006 |
| FR | 2877350 | 5/2006 |
| WO | 90/15156 | 12/1990 |
| WO | 91/00364 | 1/1991 |
| WO | 91/07424 | 5/1991 |
| WO | 93/12136 | 6/1993 |
| WO | 94/10343 | 5/1994 |
| WO | 94/10343 Cor | 5/1994 |
| WO | 94/24308 | 10/1994 |
| WO | 94/26930 | 11/1994 |

(Continued)

OTHER PUBLICATIONS

Murakami et al (Oncogene, 2006, 25:2537-2545).*
Murakami et al (Oncogene, 2006, 25:2537-2545; published online Dec. 5, 2005).*
Murakami et al (Oncogene, 2006, 25:2537-2545) Supplemental Table 1a.*
Murakami et al (Oncogene, 2006, 25:2537-2545) Supplemental Table 1 b.*

(Continued)

*Primary Examiner* — Laura B Goddard
(74) *Attorney, Agent, or Firm* — MacMillan, Sobanski & Todd, LLC

(57) ABSTRACT

The invention provides a method of determining an HCC subtype in a subject comprising a) obtaining a sample from the subject, b) assaying the sample to detect the expression of 1 or more biomarkers, and c) correlating the expression of the biomarkers with an HCC subtype in a subject. The invention further provides methods of detecting HCC stem cells in a sample. Additionally, the invention provides methods and compositions for treating subjects with HCC that take advantage of the biomarkers associated with HCC stem cells.

8 Claims, 19 Drawing Sheets

U.S. PATENT DOCUMENTS

| | | |
|---|---|---|
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 7,960,359 B2 * | 6/2011 | Brown et al. ............... 514/44 R |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer et al. |
| 2004/0033502 A1 | 2/2004 | Williams et al. |
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0127895 A1 | 6/2006 | Sabapathy |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0247448 A1 | 11/2006 | Boivin et al. |
| 2006/0292616 A1 | 12/2006 | Neely et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004322 A1 | 1/2010 | Croce |
| 2010/0048681 A1 | 2/2010 | Croce |
| 2010/0120898 A1 | 5/2010 | Croce et al. |
| 2010/0137410 A1 | 6/2010 | Croce |
| 2010/0144850 A1 | 6/2010 | Croce |
| 2010/0173319 A1 | 7/2010 | Croce et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0317610 A1 | 12/2010 | Croce |

FOREIGN PATENT DOCUMENTS

| | | |
|---|---|---|
| WO | 96/13514 | 5/1996 |
| WO | 96/35124 | 11/1996 |
| WO | 97/29119 | 8/1997 |
| WO | 98/09510 | 3/1998 |
| WO | 00/03685 | 1/2000 |
| WO | 00/50565 | 8/2000 |
| WO | 00/55169 | 9/2000 |
| WO | 00076524 | 12/2000 |
| WO | 01/44466 | 6/2001 |
| WO | 01/68666 | 9/2001 |
| WO | 01/77343 | 10/2001 |
| WO | 02/064171 | 8/2002 |
| WO | 02/064172 | 8/2002 |
| WO | 01/87958 | 11/2002 |
| WO | 03/029459 | 4/2003 |
| WO | 03029459 A2 | 4/2003 |
| WO | 03/078662 | 9/2003 |
| WO | 03/092370 | 11/2003 |
| WO | 2004/033659 | 4/2004 |
| WO | 2004/043387 | 5/2004 |
| WO | 2004/079013 | 9/2004 |
| WO | 2004/098377 | 11/2004 |
| WO | 2005/017711 | 2/2005 |
| WO | 2005/020795 | 3/2005 |
| WO | 2005060661 | 7/2005 |
| WO | 2005/078139 | 8/2005 |
| WO | 2005078139 A2 | 8/2005 |
| WO | 2005/080601 | 9/2005 |
| WO | 2005/118806 | 12/2005 |

| | | |
|---|---|---|
| WO | 2006/105486 | 10/2006 |
| WO | 2006/108718 | 10/2006 |
| WO | 2006108718 | 10/2006 |
| WO | 2006108718 A1 | 10/2006 |
| WO | 2006119266 | 11/2006 |
| WO | 2006119266 A2 | 11/2006 |
| WO | 2006/133022 | 12/2006 |
| WO | 2006/137941 | 12/2006 |
| WO | 2006133022 A2 | 12/2006 |
| WO | 2007/016548 | 2/2007 |
| WO | 2007/033023 | 3/2007 |
| WO | 2007/044413 | 4/2007 |
| WO | 2007/081680 | 7/2007 |
| WO | 2007/081720 | 7/2007 |
| WO | 2007/081740 | 7/2007 |
| WO | 2007/084486 | 7/2007 |
| WO | 2007/109236 | 9/2007 |
| WO | 2007112097 | 10/2007 |
| WO | 2007/127190 | 12/2007 |
| WO | 2008/008430 | 1/2008 |
| WO | 2008/036776 | 3/2008 |
| WO | 2008/054808 C | 5/2008 |
| WO | 2008/054828 | 5/2008 |
| WO | 2008054828 A2 | 5/2008 |
| WO | 2008/070082 | 6/2008 |
| WO | 2008/073920 | 6/2008 |
| WO | 2008073915 | 6/2008 |
| WO | 2008/094545 | 8/2008 |
| WO | 2008/097277 | 8/2008 |
| WO | 2008/136971 | 11/2008 |
| WO | 2008/153987 | 12/2008 |
| WO | 2008/157319 | 12/2008 |
| WO | 2009/018303 | 2/2009 |
| WO | 2009/020905 | 2/2009 |
| WO | 2009/026487 | 2/2009 |
| WO | 2009/033140 | 3/2009 |
| WO | 2009/049129 | 4/2009 |
| WO | 2009/055773 | 4/2009 |
| WO | 2009/064590 | 5/2009 |
| WO | 2009/070653 | 6/2009 |
| WO | 2009/100029 | 8/2009 |
| WO | 2009/108853 | 9/2009 |
| WO | 2009/108856 | 9/2009 |
| WO | 2009/108860 | 9/2009 |
| WO | 2009/108866 | 9/2009 |
| WO | 2009/152300 | 12/2009 |
| WO | 2009152300 A1 | 12/2009 |
| WO | 2010/019694 | 2/2010 |
| WO | 2010/059779 | 5/2010 |
| WO | 2010/065156 | 6/2010 |
| WO | 2010099161 | 9/2010 |

OTHER PUBLICATIONS

Akahoshi, M. et al., "Myeloproliferative Disorders Terminating in Acute Megakaryoblastic Leukemia with Chromosome 3q26 Abnormality," Cancer, 1987, pp. 2654-2661, vol. 60.
Akao, Y. et al., "let-7 MicroRNA Functions as a Potential Growth Suppressor in Human Colon Cancer Cells," Biol. Pharm. Bull., May 2006, pp. 903-906, vol. 29, No. 5.
Ambs, S. et al., "Genomic Profiling of MicroRNA and Messenger Rna Reveals Deregulated MicroRNA Expression in Prostate Cancer," Cancer Research, Aug. 2008, pp. 6162-6170, vol. 68, No. 15.
Aqeilan, R. I. et al., "Targeted Deletion of WWOX Reveals a Tumor Suppressor Function," PNAS, Mar. 2007, pp. 3949-3954, vol. 104, No. 10.
Bandres, E. et al., "Identification by Real-Time Pcr of 13 Mature MicroRNAs Differentially Expressed in Colorectal Cancer and Non-Tumoral Tissues," Molecular Cancer, Jul. 2006, 10 pp., vol. 5, No. 29.
Bartel, D. P., "MicroRNAs: Target Recognition and Regulatory Functions," Cell, Jan. 2009, pp. 215-233, vol. 136.
Bednarek, a. K. et al., "WWOX, the FRA16D Gene, Behaves as a Suppressor of Tumor Growth," Cancer Research, Nov. 2001, pp. 8068-8073, vol. 61.
Bejenaro, etal., "Ultraconserved Elements in the Human Genome," Electronic Suppl. Data, Science, 2004.
Bejerano, G. et al., "Ultraconserved Elements in the Human Genome," Science, May 2004, pp. 1321-1325, vol. 304.

Bell, D. A., "Origins and Molecular Pathology of Ovarian Cancer," Modern Pathology, 2005, pp. S19-S32, vol. 18.
Bichi, R. et al., "Human Chronic Lymphocytic Leukemia Modeled in Mouse by Targeted TCL1 Expression," PNAS, May 2002, pp. 6955-6960, vol. 99, No. 10.
Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.
Budhu, a. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.
Budhu, a. et al., "Identification of Metastasis-Related MicroRNAs in Hepatocellular Carcinoma," Hepatology, Mar. 2008, pp. 897-907, vol. 47, No. 3.
Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.
Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.
Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.
Calin, G. A. et al., "Human MicroRNA Genes are Frequently Located at Fragile Sites and Genomic Regions Involved in Cancers," PNAS, Mar. 2004, pp. 2999-3004, vol. 101, No. 9.
Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.
Calin, G. A. et al., "MicroRNA Signatures in Human Cancers," Nature Reviews Cancer, Nov. 2006, pp. 857-866, vol. 6.
Calin, G. A. et al., "MiR-15a and MiR-16-1 Cluster Functions in Human Leukemia," PNAS, Apr. 2008, pp. 5166-5171, vol. 105, No. 13.
Calin, G. A. et al., "Ultraconserved Regions Encoding ncRNAs are Altered in Human Leukemias and Carcinomas," Cancer Cell, Sep. 2007, pp. 215-229, vol. 12.
Chan, J. A. et al., "MicroRNA-21 is an Antiapoptotic Factor in Human Glioblastoma Cells," Cancer Research, Jul. 2005, pp. 6029-6033, vol. 65, No. 14.
Chang, N.-S. et al., "Molecular Mechanisms Underlying WOX1 Activation During Apoptotic and Stress Responses," Biochemical Pharmacology, 2003, pp. 1347-1354, vol. 66.
Chang, T.-C. et al., "Widespread MicroRNA Repression by Myc Contributes to Tumorigenesis," Nat Genet., Jan. 2008, pp. 43-50, vol. 40, No. 1.
Chen, C.-Z. et al., "MicroRNAs as Regulators of Mammalian Hematopoiesis," Seminars in Immunology, 2005, pp. 155-165, vol. 17.
Cheng, a. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.
Ciafre, S. A. et al., "Extensive Modulation of a Set of MicroRNAs in Primary Glioblastoma," Biochemical and Biophysical Research Communications, 2005, pp. 1351-1358, vol. 334.
Cimmino, A. et al., "miR-15 and miR-16 Induce Apoptosis by Targeting BCL2," PNAS, Sep. 2005, pp. 13944-13949, vol. 102, No. 39.
Cimmino, A. et al., Corrections to "miR-15 and miR-16 Induce Apoptosis by Targeting BCL2," PNAS, Feb. 2006, pp. 2464-2465, vol. 103, No. 7.
Costinean, S. et al., "Pre-B Cell Proliferation and Lymphoblastic Leukemia/ High-Grade Lymphoma in EμmiR155 Transgenic Mice," PNAS, May 2006, pp. 7024-7029, vol. 103, No. 18.
Croce, C. M. et al., "miRNAs, Cancer, and Stem Cell Division," Cell, 2005, pp. 6-7, vol. 36.
Croce, C. M. et al., "Role of FHIT in Human Cancer," Journal of Clinical Oncology, May 1999, pp. 1618-1624, vol. 17, No. 5.

Croce, C. M., "Causes and Consequences of MicroRNA Dysregulation in Cancer," Nature Reviews Genetics, Oct. 2009, pp. 704-714, vol. 10.

Croce, C. M., "Oncogenes and Cancer," The New England Journal of Medicine, Jan. 2008, pp. 502-511, vol. 358, No. 5.

Dalmay, T. et al., "MicroRNAs and the Hallmarks of Cancer," Oncogene, 2006, pp. 6170-6175, vol. 25.

Davies, F. E. et al., "Insights into the Multistep Transformation of Mgus to Myeloma Using Microarray Expression Analysis," Blood, Dec. 2003, pp. 4504-4511, vol. 102, No. 13.

Dohner, H. et al., "Genomic Aberrations and Survival in Chronic Lymphocytic Leukemia," The New England Journal of Medicine, Dec. 2000, pp. 1910-1916, vol. 343, No. 26.

Druck, etal., "FHIT," Atlas of Genetics and Cytogenetics in Oncology and Haematology, 2007, pp. 171-178, vol. 2.

Eis, P. S. et al., "Accumulation of miR-155 and BIC RNA in Human B Cell Lymphomas," PNAS, Mar. 2005, pp. 3627-3632, vol. 102, No. 10.

European Patent Application, EP 1795203 A2, Croce et al., Application No. 06010581.4, filed Feb. 7, 1997, published Jun. 13, 2007.

European Search Report, Application No. 06800599.0 dated Oct.19, 2009.

European Search Report, Application No. 06814375.9 dated Oct. 8, 2009.

European Search Report, Application No. 06825457.2 dated Sep. 16, 2009.

European Search Report, Application No. 07716208.9 dated Nov. 10, 2009.

European Search Report, Application No. 07717734.3 dated Nov. 9, 2009.

European Search Report, Application No. 07717903.4 dated Oct. 23, 2009.

European Search Report, Application No. 07753450.1 dated Jan.12, 2009.

European Search Report, Application No. 07810382.7 dated Sep. 14, 2009.

European Search Report, Application No. 07867402.5 dated Mar. 16, 2010.

European Search Report, Application No. 07872618.9 dated Jul. 5, 2010.

European Search Report, Application No. 08767439.6 dated May 12, 2010.

European Search Report, Application No. 08768266.2 dated Jul. 1, 2010.

European Search Report, Application No. 08796821.0 dated Aug. 4, 2010.

European Search Report, Application No. 08841700.1 dated Jun. 2, 2010.

Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.

Fabbri, M. et al., "MicroRNAs," the Cancer Journal, Jan./Feb. 2008, pp. 1-6, vol. 14, No. 1.

Fabbri, M. et al., "WWOX Gene Restoration Prevents Lung Cancer Growth in Vitro and in Vivo," PNAS, Oct. 2005, pp. 15611-15616, vol. 102, No. 43.

Fong, Y. et al., "Muir-Torre-Like Syndrome in FHIT-Deficient Mice," PNAS, Apr. 2000, pp. 4742-4747, vol. 97, No. 9.

Fox, T. et al., "A Single Amino Acid Substitution Makes ERK2 Susceptible to Pyridinyl Imidazole Inhibitors of p38 Map Kinase," Protein Science, 1998, pp. 2249-2255, vol. 7.

Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.

Garzon, R. et al., "MicroRNA Fingerprints During Human Megakaryocytopoiesis," PNAS, Mar. 2006, pp. 5078-5083, vol. 103, No. 13.

Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.

Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.

Gourley, C. et al., "WWOX Gene Expression Abolishes Ovarian Cancer Tumorigenicity in Vivo and Decreases Attachment to Fibronectin via Integrin α3," Cancer Research, Jun. 2009, pp. 4835-4842, vol. 69, No. 11.

Griffiths-Jones, S. et al., "miRBase: MicroRNA Sequences, Targets and Gene Nomenclature," Nucleic Acids Research, 2006, pp. D140-D144, vol. 34.

Guimaraes-Sternberg, C. et al., "MicroRNA Modulation of Megakaryoblast Fate Involves Cholinergic Signaling," Leukemia Research, 2006, pp. 583-595, vol. 30.

Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.

Havelange, V. et al., "MicroRNAs: New Players in Acute Myeloid Leukemia," British Journal of Cancer, 2009, pp. 743-748, vol. 101.

Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.

Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.

Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.

Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.

Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.

Iliopoulos, D. et al., "Inhibition of Breast Cancer Growth InVitro and in Vivo: Effect of Restoration of WWOX Expression," Clin. Cancer Research, Jan. 2007, pp. 268-274, vol. 13, No. 1.

Iorio, M. V. et al., "MicroRNA Gene Expression Deregulation in Human Breast Cancer," Cancer Research, Aug. 2005, pp. 7065-7070, vol. 65, No. 16.

Iorio, M. V. et al., "MicroRNA Signatures in Human Ovarian Cancer," Cancer Research, Sep. 2007, pp. 8699-8707, vol. 67, No. 18.

Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.

Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.

Ji, J. et al., "MicroRNA Expression, Survival, and Response to Interferon in Liver Cancer," The New England Journal of Medicine, Oct. 2009, pp. 1437-1447, vol. 361, No. 15.

Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.

Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.

Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.

Jiang, J. et al., "Real-Time Expression Profiling of MicroRNA Precursors in Human Cancer Cell Lines," Nucleic Acids Research, 2005, pp. 5394-5403, vol. 33, No. 17.

John, B. et al., "Human MicroRNA Targets," PLOS Biology, Nov. 2004, pp. 1862-1879, vol. 2, Issue 11.

Johnson, S. M. et al., "RAS is Regulated by the let-7 MicroRNA Family," Cell, Mar. 2005, pp. 635-647, vol. 120.

Johnson, S. M. et al., "RAS is Regulated by the let-7 MicroRNA Family," Supplemental Data, Cell, Mar. 2005, pp. 635-647, vol. 120.

Kawasaki, H. et al., "MicroRNA-196 Inhibits HOXB8 Expression in Myeloid Differentiation of HL60 Cells," Nucleic Acids Symposium Series, 2004, pp. 211-212, No. 48.

Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.

Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, 2007 Apr. 14-18, Los Angeles, CA: AACR, 2007, 2 pp., Abstract No. 1780.

Koturbash, I. et al., "Role of Epigenetic Effectors in Maintenance of the Long-Term Persistent Bystander Effect in Spleen in Vivo," Carcinogenesis, 2007, pp. 1831-1838, vol. 28, No. 8.

Krek, a. et al., "Combinatorial MicroRNA Target Predictions," Nature Genetics, May 2005, pp. 495-500, vol. 37, No. 5.

Kulshreshtha, R. et al., "A MicroRNA Signature of Hypoxia," Molecular and Cellular Biology, Mar. 2007, pp. 1859-1867, vol. 27, No. 5.

Kuroki, et al., "Genetic Alterations of the Tumor Suppressor Gene WWOX in Esophageal Squamous Cell Carcinoma," Cancer Research, Apr. 2002, pp. 2258-2260, vol. 62.

Kutay, H. et al., "Downregulation of miR-122 in the Rodent and Human Hepatocellular Carcinomas," Journal of Cellular Biochemistry, 2006, pp. 671-678, vol. 99.

Lagos-Quintana, M. et al., "New MicroRNAs From Mouse to Human," RNA, 2003, pp. 175-179, vol. 9, No. 2.

Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.

Lee, E. J. et al., "Expression Profiling Identifies MicroRNA Signature in Pancreatic Cancer," Int. J. Cancer, 2006, pp. 1046-1054, vol. 120.

Lewis, B. P. et al., "Prediction of Mammalian MicroRNA Targets," Cell, Dec. 2003, pp. 787-798, vol. 115.

Lin, R.-K. et al., "Alteration of Dna Methyltransferases Contributes to 5'CpG Methylation and Poor Prognosis in Lung Cancer," Lung Cancer, 2007, pp. 205-213, vol. 55.

Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.

Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.

Lu, J. et al., "MicroRNA Expression Profiles Classify Human Cancers," Nature, Jun. 2005, pp. 834-838, vol. 435, Supplementary Information.

Lu, J. et al., "MicroRNA Expression Profiles Classify Human Cancers," Nature, Jun. 2005, pp. 834-838, vol. 435.

Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.

Mack, G. S., "MicroRNA Gets Down to Business," Nature Biotechnology, Jun. 2007, pp. 631-638, vol. 25, No. 6.

Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.

Marcucci, et al., "MicroRNA Expression in Cytogenetically Normal Acute Myeloid Leukemia," NEJM, May 2008, pp. 1919-1928, vol. 358, No. 18.

Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pp., vol. 5, No. 24.

Mcmanus, M. T., "MicroRNAs and Cancer," Seminars in Cancer Biology, 2003, pp. 253-258, vol. 13.

Megraw, M. et al., "miRGen: A Database for the Study of Animal MicroRNA Genomic Organization and Function," Nucleic Acids Research, 2007, pp. D149-D155, vol. 35.

Meng, F. et al., "Involvement of Human MicroRNA in Growth and Response to Chemotherapy in Human Cholangiocarcinoma Cell Lines," Gastroenterology, 2006, pp. 2113-2129, vol. 130.

Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.

Michael, M. Z. et al., "Reduced Accumulation of Specific MicroRNAs in Colorectal Neoplasia," Molecular Cancer Research, Oct. 2003, pp. 882-891, vol. 1.

Miller, M. K. et al., "Concurrent Chronic Lymphocytic Leukemia Cutis and Acute Myelogenous Leukemia Cutis in a Patient with Untreated Cll," The American Journal of Dermatopathology, 2001, pp. 334-340, vol. 23, No. 4.

Mitchell, P. S. et al., "Circulating MicroRNAs as Stable Blood-Based Markers for Cancer Detection," PNAS, Jul. 2008, pp. 10513-10518, vol. 105, No. 30.

Mitrovic, T. et al., "Cancer Gene Therapy," Arch. Oncology, 2005, pp. 23-26, vol. 13, No. 1.

Mountzios, G. et al., "Mechanisms of Disease: Signal Transduction in Lung Carcinogenesis-A Comparison of Smokers and Never-Smokers," Nature Clinical Practice Oncology, Oct. 2008, pp. 610-618, vol. 5, No. 10.

Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.

Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.

Negrini, M. et al., "MicroRNAs in Human Cancer: From Research to Therapy," Journal of Cell Science, Apr. 2007, pp. 1833-1840, vol. 120.

Notice of Allowance and Fees Due in U.S. Appl. No. 12/160,064 filed Jul. 3, 2008, mailing date Nov. 29, 2009.

Notice of Allowance and Fees Due in U.S. Appl. No. 12/298,221 filed Nov. 10, 2008, mailing date Nov. 30, 2009.

Office Action issued in U.S. Appl. No. 12/083,067 filed Jun. 20, 2008, mailing date Jul. 8, 2010.

Office Action issued in U.S. Appl. No. 12/160,034 filed Jul. 3, 2008, mailing date Jun. 7, 2010.

Office Action issued in U.S. Appl. No. 12/160,061 filed Jul. 3, 2008, mailing date Mar. 12, 2010.

Office Action issued in U.S. Appl. No. 12/160,061 filed Jul. 3, 2008, mailing date Apr. 24, 2009.

Office Action issued in U.S. Appl. No. 12/160,061 filed Jul. 3, 2008, mailing date Oct. 30, 2009.

Office Action issued in U.S. Appl. No. 12/160,064 filed Jul. 3, 2008, mailing date Aug. 10, 2009.

Office Action issued in U.S. Appl. No. 12/293,471 filed Oct. 9, 2008, mailing date Jun. 8, 2010.

Office Action issued in U.S. Appl. No. 12/373,358 filed Feb. 11, 2009, mailing date Aug. 20, 2010.

Office Action issued in U.S. Appl. No. 12/442,018 filed Mar. 27, 2009, mailing date Apr. 15, 2010.

Palamarchuk, A. et al., "Akt Phosphorylates Tcl1 Oncoprotein and Inhibits Its Repressor Activity," Cancer Research, Jun. 2005, pp. 4515-4519, vol. 65, No. 11.

Pawelczyk, T. et al., "Expression in Escherichia Coli and Simple Purification of Human Fhit Protein," Protein Expr. Purlf., Apr. 2000, pp. 320-326, vol. 18, No. 3.

PCT International Preliminary Report on Patentability, PCT/US/2007/023660 filed Nov. 1, 2007, dated May 5, 2009.

PCT International Preliminary Report on Patentability, PCT/US/2008/072081 filed Aug. 4, 2008, dated Feb. 9, 2010.

PCT International Preliminary Report on Patentability, PCT/US2006/029889 filed Jul. 31, 2006, dated Feb. 5, 2008.

PCT International Preliminary Report on Patentability, PCT/US2006/035100 filed Sep. 11, 2006, dated Mar. 18, 2008.

PCT International Preliminary Report on Patentability, PCT/US2006/038824 filed Oct. 4, 2006, dated Apr. 9, 2008.

PCT International Preliminary Report on Patentability, PCT/US2007/000024 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2007/006824 filed Mar. 19, 2007, dated Sep. 23, 2008.
PCT International Preliminary Report on Patentability, PCT/US2007/009910 filed Apr. 24, 2007, dated Oct. 28, 2008.
PCT International Preliminary Report on Patentability, PCT/US2007/015892 filed Jul. 12, 2007, dated Jan. 13, 2009.
PCT International Preliminary Report on Patentability, PCT/US2007/020215 filed Sep. 17, 2007, dated Mar. 24, 2009.
PCT International Preliminary Report on Patentability, PCT/US2008/001157 filed Jan. 29, 2008, dated Aug. 4,2009.
PCT International Preliminary Report on Patentability, PCT/US2008/005503 filed Apr. 29, 2008, dated Nov. 3, 2009.
PCT International Preliminary Report on Patentability, PCT/US2008/007196 filed Jun. 9, 2008, dated Dec. 11, 2009.
PCT International Preliminary Report on Patentability, PCT/US2008/066870 filed Jun. 13, 2008, dated Dec. 17, 2009.
PCT International Preliminary Report on Patentability, PCT/US2008/071532 filed Jul. 30, 2008, dated Feb. 2, 2010.
PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Preliminary Report on Patentability, PCT/US2009/035458 filed Feb. 27, 2009, dated Aug. 31, 2010.
PCT International Preliminary Report on Patentability, PCT/US2009/035463 filed Feb. 27, 2009, dated Aug. 31, 2010.
PCT International Preliminary Report on Patentability, PCT/US2009/035470 filed Feb. 27, 2009, dated Aug. 31, 2010.
PCT International Preliminary Report on Patentability, PCT/US2009/035482 filed Feb. 27, 2009, dated Aug. 31, 2010.
PCT International Search Report and the Written Opinion, PCT/US2007/006824 filed Mar. 19, 2007, dated Mar. 3, 2008.
PCT International Search Report and the Written Opinion, PCT/US2006/29889 filed Jul. 31, 2006, dated Jul. 10, 2007.
PCT International Search Report and the Written Opinion, PCT/US2006/35100 filed Sep. 11, 2006, dated Sep. 5, 2007.
PCT International Search Report and the Written Opinion, PCT/US2006/38824 filed Oct. 4, 2006, dated Aug. 9, 2007.
PCT International Search Report and the Written Opinion, PCT/US2007/00024 filed Jan. 3, 2007, dated Nov. 5, 2007.
PCT International Search Report and the Written Opinion, PCT/US2007/00103 filed Jan. 3, 2007, dated Dec. 3, 2007.
PCT International Search Report and the Written Opinion, PCT/US2007/00159 filed Jan. 3, 2007, dated Apr. 11, 2008.
PCT International Search Report and the Written Opinion, PCT/US2007/006824 filed Mar. 19, 2007, dated May 14, 2008.
PCT International Search Report and the Written Opinion, PCT/US2007/09910 filed Apr. 24, 2007, dated Feb. 13, 2008.
PCT International Search Report and the Written Opinion, PCT/US2007/15892 filed Jul. 12, 2007, dated Sep. 30, 2008.
PCT International Search Report and the Written Opinion, PCT/US2007/20215 filed Sep. 17, 2007, dated Jul. 25, 2008.
PCT International Search Report and the Written Opinion, PCT/US2007/23660 filed Nov. 1, 2007, dated Sep. 16, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.
PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2008/72081 filed Aug. 4,2008, dated Jan. 14, 2009.
PCT International Search Report and the Written Opinion, PCT/US2008/73964 filed 22 Aug. 2008, dated 24 Dec. 2008.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/81294 filed Oct. 27, 2008, dated Mar. 26, 2009.
PCT International Search Report and the Written Opinion, PCT/US2008/84821 filed Nov. 26, 2008, dated Feb. 17, 2009.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2009/38214 filed Mar. 25, 2009, dated Aug. 14, 2009.
PCT International Search Report and the Written Opinion, PCT/US2009/46999 filed Jun 11, 2009, dated Nov. 23, 2009.
PCT International Search Report and the Written Opinion, PCT/US2009/53586 filed Au. 12, 2009, dated Oct. 28, 2009.
PCT International Search Report and the Written Opinion, PCT/US2009/65072 filed Nov. 19, 2009, dated Mar. 3, 2010.
PCT International Search Report and the Written Opinion, PCT/US2010/025173 filed Feb. 24, 2010, dated Jul. 6, 2010.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Animal Models for Chronic Lymphocytic Leumekia," Journal of Cellular Biochemistry, 2007, pp. 1109-1118, vol. 100.
Pekarsky, Y. et al., "Tcl1 Enhances Akt Kinase Activity and Mediates Its Nuclear Translocation," Pnas, Mar. 2000, pp. 3028-3033, vol. 97, No. 7.
Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.
Pekarsky, Y. et al., "Tcl1 Functions as a Transcriptional Regulator and is Directly Involved in the Pathogenesis of Cll," Pnas, Dec. 2008, pp. 19643-19648, vol. 105, No. 50.
Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.
Prueitt, R. L. et al., "Expression of MicroRNAs and Protein-Coding Genes Associated with Perineural Invasion in Prostate Cancer," the Prostate, 2008, pp. 1152-1164, vol. 68.
Qin, H. R. et al., "A Role for the Wwox Gene in Prostate Cancer," Cancer Research, Jul. 2006, pp. 64776481, vol. 66, No. 13.
Ramkissoon, S. H, et al., "Hematopoietic-Specific MicroRNA Expression in Human Cells," Leukemia Research, 2006, pp. 643-647, vol. 30.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.
Rozovskaia, T. et al., "Expression Profiles of Acute Lymphoblastic and Myeloblastic Leukemias with All-1 Rearrangements," PNAS, Jun. 2003, pp. 7853-7858, vol. 100, No. 13.
Schetter, a. J. et al., "MicroRNA Expression Profiles Associated With Prognosis and Therapeutic Outcome in Colon Adenocarcinoma," JAMA, Jan. 2008, pp. 425-436, vol. 299, No. 4.
Schmittgen, T. D. et al., "A High-Throughput Method to Monitor the Expression of MicroRNA Precursors," Nucleic Acids Research, Feb. 2004, vol. 32, No. 4.

Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.

Seike, M. et al., "MiR-21 is an EGFR-Regulated Anti-Apoptotic Factor in Lung Cancer in Never-Smokers," Supporting Information, PNAS, Jul. 2009, pp. 12085-12090. vol. 106, No. 29.

Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.

Seth, P., "Vector-Mediated Cancer Gene Therapy," Cancer Biology & Therapy, May 2005, pp. 512-517, vol. 4, Issue 5.

Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.

Sharma, S. et al., "Development of Inhalational Agents for Oncologic Use," Journal of Clinical Oncology, Mar. 2001, Abstract, vol. 19, Issue 6.

Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.

Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.

Tang, X. et al., "A Simple Array Platform for MicroRNA Analysis and Its Application in Mouse Tissues," RNA, Aug. 2007, pp. 1-20, vol. 13.

Thomson, J. M. et al., "A Custom Microarray Platform for Analysis of MicroRNA Gene Expression," Nature Methods, Oct. 2004, pp. 1-7, vol. 1, No. 1.

Thorgeirsson, S. S. et al., "Functional Genomics of Hepatocellular Carcinoma," Hepatology, Feb. 2006, pp. S145-S150, vol. 43, No. 2, Suppl. 1.

Tockman, M. S. et al., "Considerations in Bringing a Cancer Biomarker to Clinical Application," Cancer Research, May 1992, pp. 2711s-2718s, vol. 52.

Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.

Tricoli, J. V. et al., "MicroRNA: Potential for Cancer Detection, Diagnosis, and Prognosis," Cancer Research, May 2007, pp. 4553-4555, vol. 67, No. 10.

Ueda, T. et al., "Relation Between MicroRNA Expression and Progression and Prognosis of Gastric Cancer: A MicroRNA Expression Analysis," Published Online; www.thelancet.com/oncology, Dec. 2009, D01:10.1016/S1470-2045(09)70343-2.

Valeri, N. et al., "Epigenetics, miRNAs, and Human Cancer: a New Chapter in Human Gene Regulation," Mamm Genome, Aug. 2009, pp. 573-580, vol. 20.

Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.

Virgilio, L. et al., "Identification of the TCL1 Gene Involved in T-Call Malignancies," Proc. Natl. Acad. Sci., Dec. 1994, pp. 12530-12534, vol. 91.

Visone, R. et al., "MiRNAs and Cancer," the American Journal of Pathology, Apr. 2009, pp. 1131-1138, vol. 174, No. 4.

Volinia, et al., "Reprogramming of MirRNA Networks in Cancer and Leukemia," Genome Research, 2010, pp. 589-599, vol. 20.

Volinia, S. et al., "A MicroRNA Expression Signature of Human Solid Tumors Defines Cancer Gene Targets," PNAS, Feb. 2006, pp. 2257-2261, vol. 103, No. 7.

Wang, E. et al., "Ontogeny and Oncogenesis Balance the Transcriptional Profile of Renal Cell Cancer," Cancer Research, Oct. 2004, pp. 7279-7287, vol. 64.

Wang, X. et al., "Association Between CpG Island Methylation of the WWOX Gene and Its Expression in Breast Cancers," Tumor Biology, Feb. 2009, pp. 8-14, vol. 30.

Weidhaas, J., "Using MicroRNAs to Understand Cancer Biology," Published Online Dec. 21, 2009, DOI: 10.1016/S1470-2045(09)70386-9.

Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.

Yamashita, T. et al., "EpCAM and a-Fetoprotein Expression Defines Novel Prognostic Subtypes of Hepatocellular Carcinoma," Cancer Research, Mar. 2008, pp. 1451-1461, vol. 68, No. 5.

Yanaihara, N. et al., "Unique MicroRNA Molecular Profiles in Lung Cancer Diagnosis and Prognosis," Cancer Cell, Mar. 2006, pp. 189-198, vol. 9.

Yang, J. et al., "Analysis of Sequence Variations in 59 MicroRNAs in Hepatocellular Carcinomas," Mutation Research, Aug. 2008, pp. 205-209, vol. 638.

Yendamuri, S. et al., "WW Domain Containing Oxidoreductase Gene Expression is Altered in Non-Small Cell Lung Cancer," Cancer Research, Feb. 2003, pp. 878-881, vol. 63.

Yoon, S. et al., "Prediction of Regulatory Modules Comprising MicroRNAs and Target Genes," Bioinformatics Genes and Genomes, 2005. Pages ii93-ii100, vol. 21, Suppl. 2.

Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," the Journal of Biological Chemisty, Jul. 2004, pp. 41377-41383, vol. 279, No. 40.

Zeng, Y. et al., "Recognition and Cleavage of Primary MicroRNA Precursors by the Nuclear Processing Enzyme Drosha," the EMBO Journal, 2005, pp. 138-148, vol. 24.

Zhang, L. et al., "Genomic and Epigenetic Alterations Deregulate MicroRNA Expression in Human Epithelial Ovarian Cancer," PNAS, May 2008, pp. 7004-7009, vol. 105, No. 19.

Zhang, L. et al., "MicroRNAs Exhibit High Frequency Genomic Alterations in Human Cancer," PNAS, Jun. 2006, pp. 9136-9141, vol. 103, No. 24.

Zhang, L. et al., Supporting Information, PNAS 2008, pp. 1-11.

Zhang, Z. et al., "Three Biomarkers Identified from Serum Proteomic Analysis for the Detection of Early Stage Ovarian Cancer," Cancer Research, Aug. 2004, pp. 5882-5890, vol. 64.

Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.

Ambros, V. et al., "A Uniform System for MicroRNA Annotation," RNA, 2003, pp. 277-279, vol. 9.

Baira, E. et al., "Ultraconserved Elements: Genomics, Function and Disease," RNA Biology, Jul. 2008, pp. 132-134, vol. 5, No. 3.

Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.

Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.

Boland, C.R. et al., "Lynch Syndrome: Form, Function, Proteins, and Basketball," Gastroenterology, Aug. 2005, pp. 751-755, vol. 129, No. 2.

Caldas, C. et al., "Sizing Up miRNAs as Cancer Genes," Nature Medicine, Jul. 2005, pp. 712-714, vol. 11, No. 7.

Canadian Intellectual Property Office, Requisition by the Examiner, Application No. 2,635,616, Dated Feb. 21, 2011.

Canadian Office Action, Application No. 2,617,581, dated 01 Feb. 2011.

Canadian Office Action, Application No. 2,621,441, dated 01 Feb. 2011.

Castoldi, M. et al., "A Sensitive Array for MicroRNA Expression Profiling (miChip) Based on Locked Nucleic Acids (LNA)," RNA, 2006, pp. 913-920, vol. 12.

Chinese Office Action, Application No. 200680036598.3 dated 24 Feb. 2011.

Chinese Office Action, Application No. 200780040146.7 dated 25 May 2011.

Cui, S. et al., "MicroRNAs that Underlie Ovarian Cancer Development and Response to Chemotherapy," 98th AACR Annual Meeting, Apr. 14-18, 2007, Los Angeles, CA.

Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.

Ep Search Report, Application No. 08782609.5 dated Oct. 28, 2010.

Esquela-Kerscher, a. et al., "Oncomirs—MicroRNAs with a Role in Cancer," Nature Reviews:Cancer, Apr. 2006, pp. 259-269, vol. 6.

European Communication Pursuant to Article 94(3) EPC, Application No. 07810382.7, dated Dec. 8, 2010.

European Communication Pursuant to Article 94(3) EPC, Application No. 07867402.5, dated Jan. 5, 2011.

European Communication Pursuant to Article 94(3) EPC, Application No. 08768266.2, dated Apr. 18, 2011.

European Search Reoprt, Application No. 08841700.1, dated Jan. 4, 2011.

European Search Report, Application No. 08798444.9-2402, PCT/US2008/073964, dated Dec. 16, 2010.

European Search Report, Application No. 08799295.4-2402, PCT/US2008/075565, dated Nov. 9, 2010.

European Supplementary Search Report, Application No. 09715064.3 dated 24 May 2011.

Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.

Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.

Ford, L.P., "A MicroRNA Expression Signature of Human Solid Tumors Defines Cancer Gene Targets," Leukemia Research, 2006, pp. 511-513, vol. 30.

Garofalo, M. et al., "miR-221&222 Regulate Trail Resistance and Enhance Tumorigenicity through PTEN and TIMP3 Downregulation," Cancer Cell, Dec. 2009, pp. 498-509, vol. 16.

Garzon, R. et al., "MicroRNA Expression and Function in Cancer," TRENDS in Molecular Medicine, Oct. 2006, pp. 580-587, vol. 12, No. 12.

Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.

Griffths-Jones, S. et al., "miRBase: Tools for MicroRNA Genomics," Nucleic Acids Research, 2008, pp. D154-D157, vol. 36.

Griffths-Jones, S., "The MicroRNA Registry," Nucleic Acids Research, 2004, pp. D109-D111, vol. 32.

He, X. et al., "MicroRNA and Esophageal Carcinoma," Journal of Nanjing Medical University, 2007, pp. 201206, vol. 21, No. 4.

Ishii, H. et al., "Effect of Adenoviral Transduction of the Fragile Histidine Triad Gene into Esophageal Cancer Cells," Cancer Research, Feb. 2001, pp. 1578-1584, vol. 61.

Kelly, L.M. et al., "CT53518, A Novel Selective FLT3 Antagonist for the Treatment of Acute Myelogenous Leukemia (AML)," Cancer Cell, Jun. 2002, pp. 421-432, vol. 1.

Kozomara, A. et al., "miRBase: Integrating MicroRNA Annotation and Deep-Sequencing Data," Nucleic Acids Research, 2011, pp. D152-D157, vol. 39.

Lagos-Quintana, M. et al., "Identification of Tissue-Specific MicroRNAs from Mouse," Current Biology, Apr. 2002, pp. 735-739, vol. 12.

Landgraf, P. et al., "A Mammalian MicroRNA Expression Atlas Based on Small RNA Library Sequencing," Cell, Jun. 2007, pp. 1401-1414, vol. 129.

Lanza, G. et al., "mRNA/microRNA Gene Expression Profile in Microsatellite Unstable Colorectal Cancer," Molecular Cancer, 2007, pp. 1-11, vol. 6, No. 54.

Li, S.-C. et al., "Bioinformatic Discovery of MicroRNA Precursors from Human ESTs and Introns," BMC Genomics, 2006, vol. 7.

Lujambio, A. et al., "A MicroRNA Dna Methylation Signature for Human Cancer Metastasis," PNAS, Sep. 2008, pp. 13556-13561, vol. 105, No. 36.

Medina, P.P. et al., "OncomiR Addiction in an in Vivo Model of MicroRNA-21-Induced Pre-B-Cell Lymphoma," Nature Letters, Sep. 2010, pp. 86-91, vol. 467.

Medina, P.P., "OncomiR Addicton in an in vivo Model of Micro-Rna-21-Induced Pre-B-Cell Lymphoma," Supplementary Information, Sep. 2010, p. 1-22.

Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.

Nicoloso, M.S. et al., "MicroRNAs—The Micro Steering Wheel of Tumour Metastases," Nature Reviews: Cancer, Apr. 2009, pp. 293-302, vol. 9.

Nurden, A.T., "Qualitative Disorders of Platelets and Megakaryocytes," Journal of Thrombosis and Haemostasis, 2005, vol. 3, pp. 1773-1782.

Pichiorri, F. et al., "MicroRNAs Regulate Critical Genes Associated with Multiple Myeloma Pathogenesis," PNAS, Sep. 2008, pp. 12885-12890, vol. 105, No. 35.

Pineau, P. et al., "miR-221 Overexpression Contributes to Liver Tumorigenesis," PNAS, Jan. 2010, pp. 264-269, vol. 107, No. 1.

Porkka, K.P. et al., "MicroRNA Expression Profiling in Prostate Cancer," Cancer Research, 2007, pp. 61306135, vol. 67, No. 13.

Pruitt, K.D. et al., "NCBI Reference Sequence (RefSeq): a Curated Non-Redundant Sequence Database of Genomes, Transcripts and Proteins," Nucleic Acids Research, 2005, pp. D501-D504, vol. 33.

Saini, H. K. et al., "Annotation of Mammalian Primary MicroRNAs," BMC Genomics, 2008, vol. 9.

Santanam, U. et al., "Chronic Lymphocytic Leukemia Modeled in Mouse by Targeted miR-29 Expression," PNAS, Jul. 2010, pp. 12210-12215, vol. 107, No. 27.

Sasaki, Y.T.F. et al., "Coordinated Expression of ncRNAs and HOX mRNAs in the Human HOXA Locus," Biochemical and Biophysical Communications, 2007, pp. 724-730, vol. 357.

Schagen, F. et al., "Genetic Targeting of Adenovirus Vectors Using a Reovirus Sigmal-Based Attachment Protein," Molecular Therapy, May 2006, pp. 997-1005, vol. 13, No. 5.

Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.

Slack, F.J., "Big Roles for Small RNAs," Nature, Feb. 2010, p. 616, vol. 463.

Suarez-Saiz, F.J. et al., "MicroRNA Expression Profiling in Acute Myelogenous Leukemia," Canada Blood, Nov. 2004, Abstract #1131, p. 320A.

Taccioli, C. et al., "Ucbase & miRfunc: A Database of Ultraconserved Sequences and MicroRNA Function," Nucleic Acids Research, 2009, pp. D41-D48, vol. 37.

Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.

Valeri, N. et al., "Modulation of Mismatch Repair and Genomic Stability by miR-155," PNAS, Apr. 2010, pp. 6982-6987, vol. 107, No. 15.

Wijermans, P.W., "Low Dose Azanucleosidesfor High Risk (s) MDS and AML," Haematologica Reports,Nov. 2006, pp. 74-76. vol. 2, Issue, 15.

Zawacka-Pankau, J. et al., "Expression and Simple, One-Step Purification of Fragile Histidine Triad (Fhit) Tumor Suppressor Mutant Forms in Escherichia Coli and their Interaction with Protoporphyrin IX," Biotechnology Letters, Jun. 2007, pp. 877-883, vol. 29, No. 6.

European Communication Pursuant to Article 94(3) EPC, Application No. 08767439.9, dated Mar. 15, 2011.

European Seach Report, Application No. 11151749.6, dated Feb. 8, 2011.

European Search Report, Application No. 11151769-4, dated Feb. 8, 2011.

European Search Report, Application No. 11151771-0, dated Feb. 8, 2011.

European Search Report, Application No. 11151772-8, dated Feb. 8, 2011.

Chinese Office Action, Application No. 200680039776.8 dated Jun. 30, 2011.

Australian Office Action, Application No. 2006291165 dated Aug. 23, 2011.
European Search Report, Application No. 09713926.5 dated Jul. 21, 2011.
PCT International Preliminary Report on Patentability, PCT/US2010/025173 filed Feb. 24, 2010, dated Sep 9, 2011.
European Search Report, Application No. 08713330.2, dated Jul. 22, 2011.
European Search Report, Application No. 09714868.8 dated Aug. 1, 2011..
PCT International Preliminary Report on Patentability, PCT/US2009/065072 filed Nov. 19, 2009, dated Jun. 3, 2011.
Chinese Office Action, Application No. 200780005821.2 dated Jan. 26, 2011.
PCT International Preliminary Report on Patentability, PCT/US2009/03814 filed Mar. 25, 2009, dated Jun. 16, 2011.
Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.
Cannistra, S.A., "Cancer of the Ovary," the New England Journal of Medicine, 2004, pp. 2519-2529, vol. 351, No. 25.
Chim, S.S.C. et al., "Detection and Characterization of Placental MicroRNAs in Maternal Plasma," Clinical Chemistry, 2008, pp. 482-490, vol. 54, No. 3.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912916, vol. 21.
Feng, G. et al., "Elevated Serum-Circulating Rna in Patients with Conventional Renal Cell Cancer," Anticancer Research, 2008, pp. 321-326, vol. 28.
He, L. et al., "A MicroRNA Polycistron as a Potential Human Oncogene," Nature, Jun. 2005, pp. 828-833, vol. 435.
Jacobs, I.J. et al. "Prevalence Screening for Ovarian Cancer in Postmenopausal Women by CA 125 Measurement and Ultrasoundography, " BMJ, Apr. 1993, pp.1030-1034, vol. 306.
Jacobs, I.J. et al., "Progress and Challenges in Screening for Early Detection of Ovarian Cancer," Molecular & Cellular Proteomics, 2004, pp. 355-366, vol. 3.
Jemal, A. et al., "Cancer Statistics, 2008," CA Cancer J. Clin., 2008, pp. 71-96, vol. 58, No. 2.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Mendell, J.T., "miRiad Roles for the miR-17-92 Cluster in Development and Disease," Cell, 2008, pp. 217-.
Meng, F. et al., "MicroRNA-21 Regulates Expression of the Pten Tumor Suppressor Gene in Human Hepatocellular Cancer," Gastroenterology, 2007, pp. 647-658, vol. 133.
Nam, E.J. et al., "MicroRNA Expression Profiles in Serous Ovarian Carcinoma," Clinical Cancer Research, 2008, pp. 2690-2695, vol. 14, No. 9.
Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.
Petrocca, F. et al., "MicroRNAs Deregulation in Gastric Cancer," PNAS, Apr. 2006, p. 1338, vol. 47, Abstract # 5690.
Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.
Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.
Thomson, M., Supplementary data for " A Custon Microarray Platform for Analysis of MicroRNA Gene Expression," Nature Methods, Oct. 2004, pp. 47-53, vol. 1, No. 1.
Tilt, E. et al., "Expression and Function of Micro RNAs in Immune Cells During Normal or Disease State," International Journal of Medicine Sciences, 2008, pp. 73-79, vol. 5, No. 2.
Verschuur, a.C., "Acute Megakaryoblastic Leukemia," May 2004, pp. 1-5, Retrieved from the Internet: URL:http://www.orpga.net/data/patho/GB/uk-AMLM7.pdf.
Budhu, A. et al, "Identification of Metastasis-Related MicroRNAs in Hepatocellular Carcinoma," Hepatology, Mar. 2008, pp. 897-907, vol. 47, No. 3, XP-002551540.
Budhu, A. et al., "A Unique Metastasis-Related MicroRNA Expression Signature is a Prognostic Indicator of Survival and Recurrence in Hepatocellular Carcinoma," Abstract Hepatology, 2007, p. 791A, vol. 46, No. 4, Supplement 1, XP-002554084.
Chang, T.-C. et al., "Widespread MicroRNA Repression by Myc Contributes to Tumorigenesis," Nature Genetics, Jan. 2008, pp. 43-50, vol. 40, No. 1.
Ji, J. et al., "MicroRNA Expression, Survival, and Response to Interferon in Liver Cancer," the New England Journal of Medicine, Oct. 2009, pp. 1437-1447, vol. 361.
Ji, J. et al., "New Kids on the Block," Cancer Biology & Therapy, Aug. 2009, pp. 1-8, vol. 8, Issue 16.
Jiang, J. et al., "Real-Time Expression Profiling of MicroRNA Precursors in Human Cancer Cell Lines," Nucleic Acids Research, 2005, pp. 5394-5403, vol. 33, No. 7.
Kotoula, V. et al., "In Situ Detection of MicroRNAs 146b, 221 and 222 in Human Carcinoma Tissues Reveals Tumor-Type Specific Expression Patterns," AACR Annual Meeting, Apr. 14-18, 2007, Los Angeles, CA, XP-008123614.
Kutay, H. et al., "Downregulation of miR-122 in the Rodent and Human Hepatocellular Carinomas," Journal of Cellular Biochemistry, 2006, pp. 671-678, vol. 99.
Lu, J. et al., "MicroRNA Expression Profiles Classify Human Cancers," Nature, Jun. 2005, pp. 834-838, vol. 435, XP-002339403.
Murakami, Y. et al., "Comprehensive Analysis of MicroRNA Expression Patterns in Hepatocellular Carcinoma and Non-Tumorous Tissues," Oncogenomics, 2006, pp. 2537-2545, vol. 25, XP-002529509.
Pedersen, I. et al., "Interferon Modulation of Cellular MicroRNAs as an Antiviral Mechanism," Nature, Oct. 2007, pp. 919-923, vol. 449.
Thorgeirsson, S. et al., "Functional Genomics of Hepatocellular Carcinoma," Hepatology, 2006, pp. S145-S150, vol. 43, XP-002554083.
Yamashita, T. et al., "Activation of Hepatic Stem Cell Marker EpCAM by Wnt-β-Catenin Signaling in Hepatocellular Carcinoma," Cancer Research, 2007, pp. 10831-10839, vol. 67.
Yanaihara, N. et al., "Unique MicroRNA Molecular Profiles in Lung Cancer Diagnosis and Prognosis," Cancer Cell, Mar. 2006, pp. 189-198, vol. 9, XP-002510059.
PCT International Search Report and the Written Opinion, PCT/US07/23660 filed Nov. 1, 2007, dated Sep. 16, 2008.
PCT International Search Report and the Written Opinion, PCT/US08/07196 filed Jun. 9, 2008, dated Nov. 19, 2008.
PCT International Search Report and the Written Opinion, PCT/US09/46999 filed Jun. 11, 2009, dated Nov.23, 2009.
EP Communication, Application No. 08768266.2-2402/2152900, dated Jan. 7, 2010.

* cited by examiner

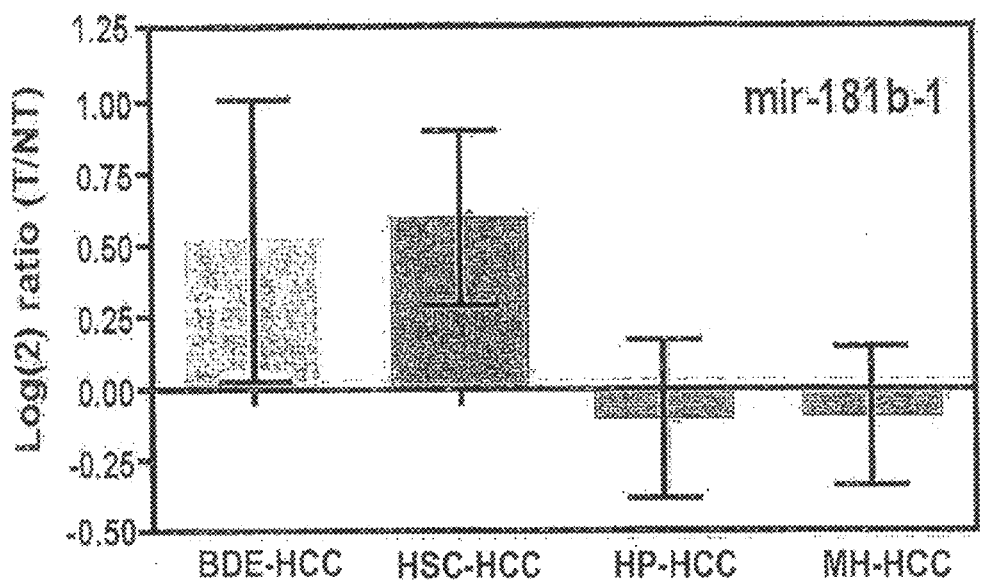
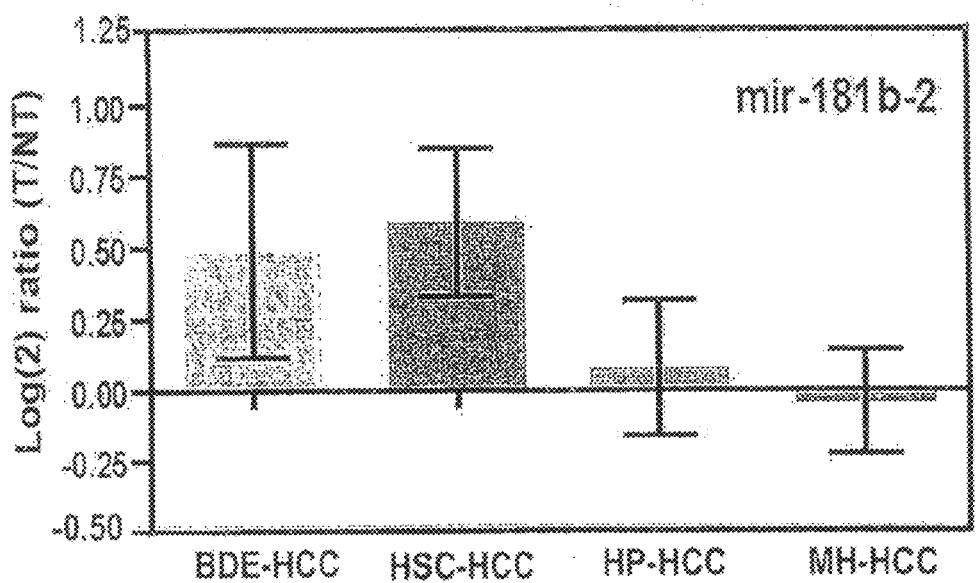

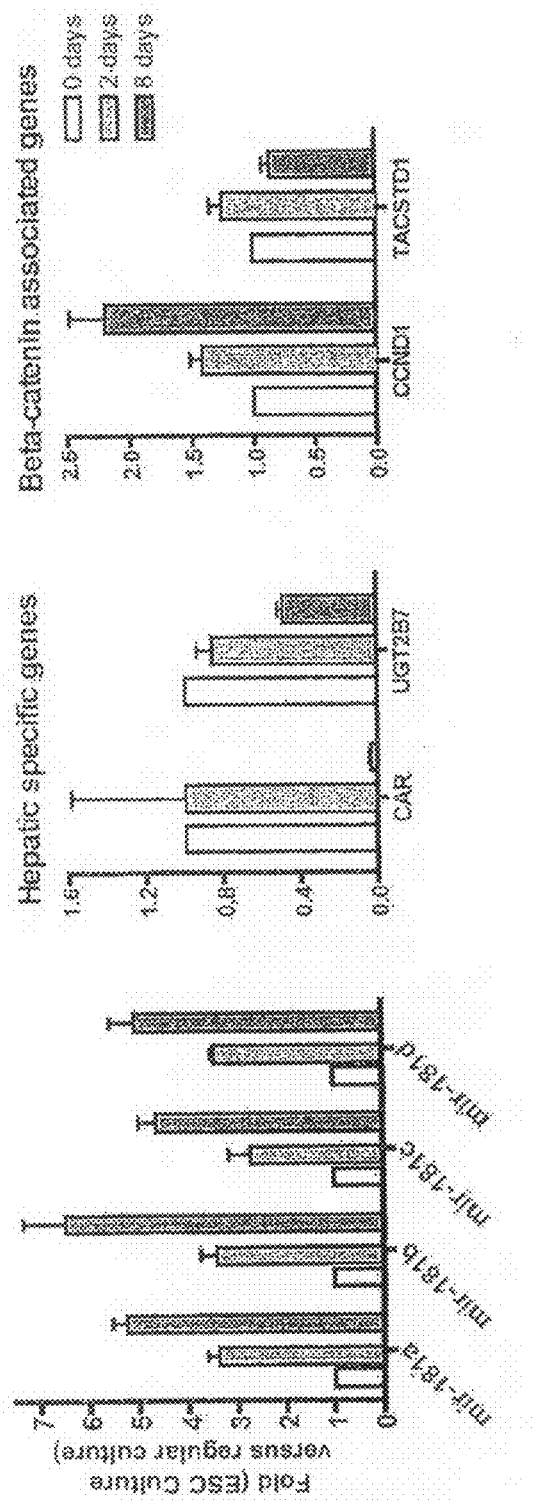

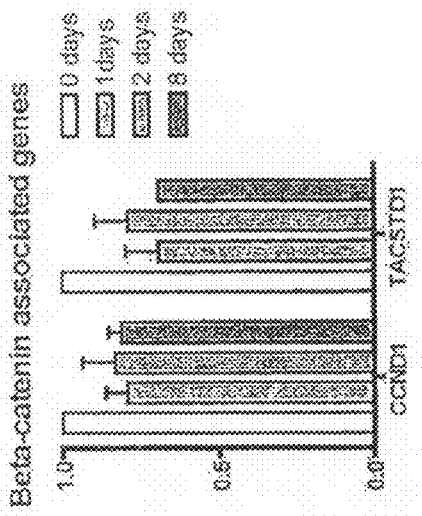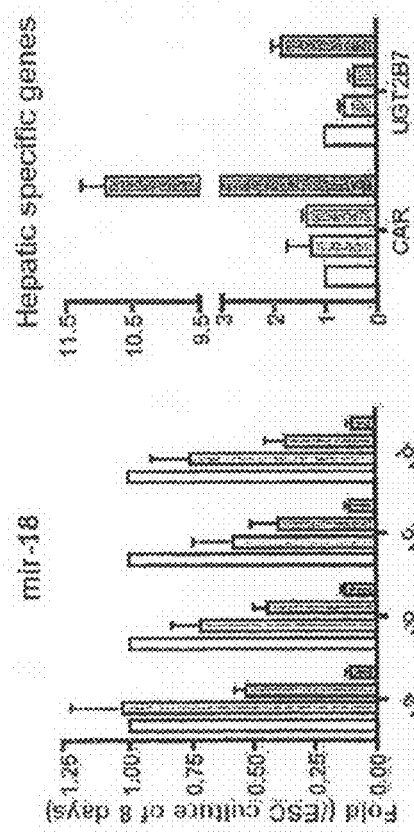

FIG. 7A

POSITION 611-632 OF DKK1 3'UTR

```
----AAUGAUCAU-AGCACC-UUGGAUG----     DKK1
    | . ||| . .|| |  |||.|||
    UG--AGUGGCUGUCGCAACUUACAA         mir-181a ----AAUGAUCAUA-GCACC-UUGGAUG----     DKK1
    .  .||.  .|| |   ||.|||
    G--GGUGGCUGUCGUUACUUACAA          mir-181b ----AAUGAUCA-UAGCACCUUGGAUG----      DKK1
    |.  ||| . .||   |||.|||
    UG--AGUGGCUGUCCAACUUACAA          mir-181c ----AAUGAUCAUA-GCACC-UUGGAUG----     DKK1
    ||. .||. .|| |   ||.|||
    UUG--GGUGGCUGUUGUUACUUACAA        mir-181d
```

FIG. 7B

POSITION 771-799 OF DKK1 3'UTR

```
----AACCUGUCCUGAAAGAAGGUCAAGUGUGU----     DKK1
    ||  ...|   | ||  | |  |.||| |
    UGAGUGGC--UGUCG-CAAC-UUACA-A          mir-181a ----AACCUGUCCUGAAAGAAGGUCAAGUGUGU----     DKK1
    ||...|   || ||   ..|  |.|| | |
    GGGUGG--CUGUCG-UUAC-UUACA-A           mir-181b ----AACCUGUCCUGAAAGAAGGUCAAGUGUGU----     DKK1
    || ...|   ||     ||||  |.||| |
    UGAGUGG--CUG---UCCAACUUACA-A          mir-181c ----AACCUGUCC-UGAAAGAAGGUCAAGUGUGU----    DKK1
    ||||...|  ..|   || |  |.||| |
    UUGGGUGGCUGUUG--UU--A-CUUACA-A        mir-181d
```

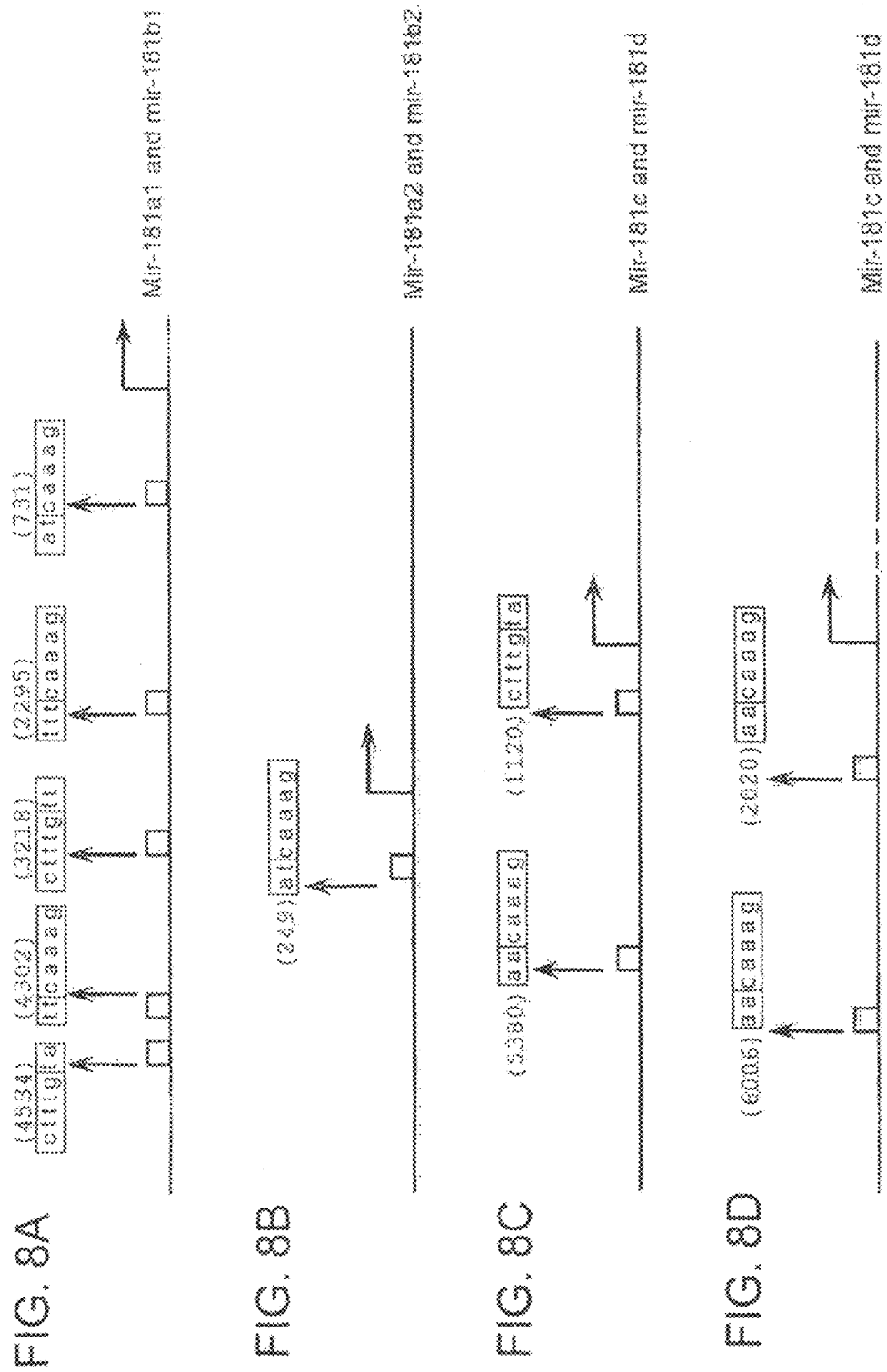

METHODS FOR DETERMINING HEPTOCELLULAR CARCINOMA SUBTYPE AND DETECTING HEPATIC CANCER STEM CELLS

SEQUENCE LISTING

The instant application contains a Sequence Listing which has been submitted in ASCII format via EFS-Web and is hereby incorporated by reference in its entirety. Said ASCII copy, created on Sep. 20, 2012, is named 604_50243_SEQ_LIST_OSU-2006-027-2.txt and is 6,868 bytes in size.

BACKGROUND OF THE INVENTION

Hepatocellular carcinoma (HCC) is the third leading cause of cancer death world-wide. HCC is very heterogeneous in terms of its clinical presentation and genomic and transcriptomic patterns. The heterogeneity in HCC and lack of appropriate biomarkers for its detection and subtype identification has hampered patient prognosis and treatment stratification.

Accordingly, there is a desire for one or more biomarkers that can identify the subtype of HCC in a mammal, as well as methods of providing appropriate treatment based on the subtype of HCC.

BRIEF SUMMARY OF THE INVENTION

The invention provides a method of determining the subtype of HCC in a subject, the method comprising a) obtaining a sample from the subject, b) assaying the sample to detect at least 1 biomarkers, and c) correlating the biomarkers detected with an HCC subtype in the subject. In this regard, the biomarkers are selected from the group consisting of the biomarkers identified by SEQ ID NOs: 1-39.

The invention also provides a method of detecting a HCC stem cell in a sample. In one embodiment the inventive method comprises a) obtaining a sample, b) assaying the sample to detect the presence of a mir-181 biomarker, and c) correlating the presence or absence of the mir-181 biomarker with the presence or absence of the HCC stem cell in the sample.

The invention also provides methods and compositions for treating subjects with HCC that take advantage of the biomarkers associated with HCC stem cells.

BRIEF DESCRIPTION OF THE SEVERAL VIEWS OF THE DRAWINGS

FIG. 1C shows the expression of mir-181b1 in log(2) ratio (of tumor to nontumor tissue) in HSC, DBE, HP, and MH-HCC cells based on microRNA analysis.

FIG. 1D shows the expression of mir-181b2 in log(2) ratio (of tumor to nontumor tissue) in HSC, DBE, HP, and MH-HCC cells based on microRNA analysis.

FIG. 3A a graph showing the fold production of the mir-181a, mir-181b, mir-181c, and mir-181d at 0, 2, and 8 days in ESC media versus regular culture.

FIG. 3B is a graph showing the fold of the CAR and UGT2B7 at 0, 2, and 8 clays in ESC media versus regular culture.

FIG. 3C a graph showing the fold production of CCND1 and TACSTD1 at 0, 2, and 8 days in ESC media versus regular culture.

FIG. 3D a graph showing the fold production of the mir-181a, mir-181b, mir-181c, and mir-181d at 0, 1, 2, and 8 days following withdrawal of ESC media.

FIG. 3E a graph showing the fold production of CAR and UGT2B7 at 0, 1, 2, and 8 days following withdrawal of ESC media.

FIG. 3F a graph showing the fold production of CCND1 and TCSTD1 at 0, 1, 2, and 8 days following withdrawal of ESC media.

FIG. 7A shows the predicted binding site of mir-181a (SEQ ID NO: 41), mir-181b (SEQ ID NO: 42), mir-181c (SEQ ID NO: 43), and mir-181d (SEQ ID NO: 44) at the 611-632 3'-UTR of DKK1 (SEQ ID NO: 40).

FIG. 7B shows predicted binding sites of mir-181a (SEQ ID NO: 41), mir-181b (SEQ ID NO: 42), mir-181c (SEQ ID NO: 43), and mir-181d (SEQ ID NO: 44) at the 771-799 3'-UTR of DKK1 (SEQ ID NO: 45).

FIG. 8A is a predicted TCF-4 binding site for mir-181a1 and mir-181b1.

FIG. 8B is a predicted TCF-4 binding site for mir-181a2 and mir-181b2.

FIG. 8C is a predicted TCF-4 binding site for mir-181c and mir-181d.

FIG. 8D is another predicted TCF-4 binding site for mir-181c and mir-181d.

DETAILED DESCRIPTION OF THE INVENTION

Figure 1A:
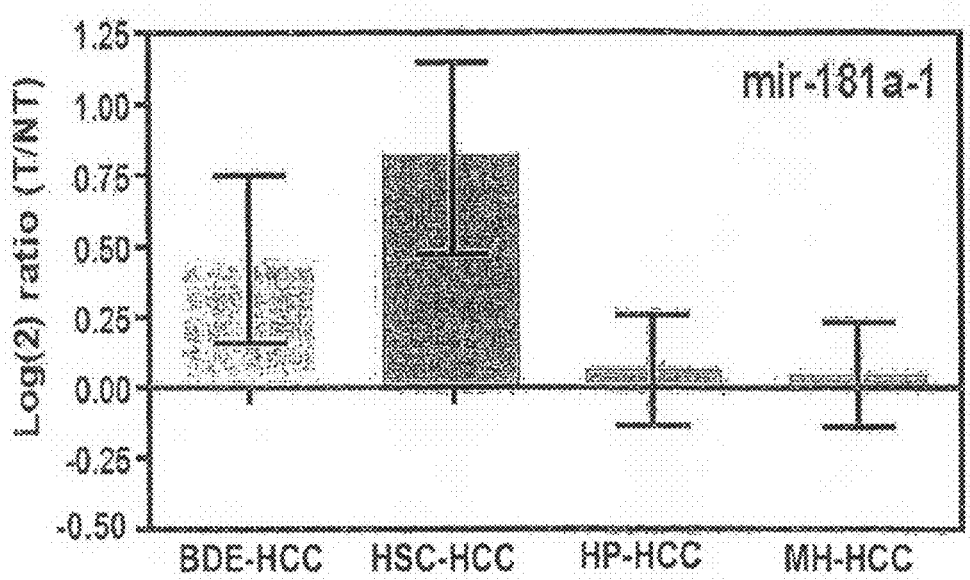
FIG. 1A shows the expression of mir-181a1 in log(2) ratio (of tumor to nontumor tissue) in HSC-HCC cells based on microRNA analysis.
Figure 1B:
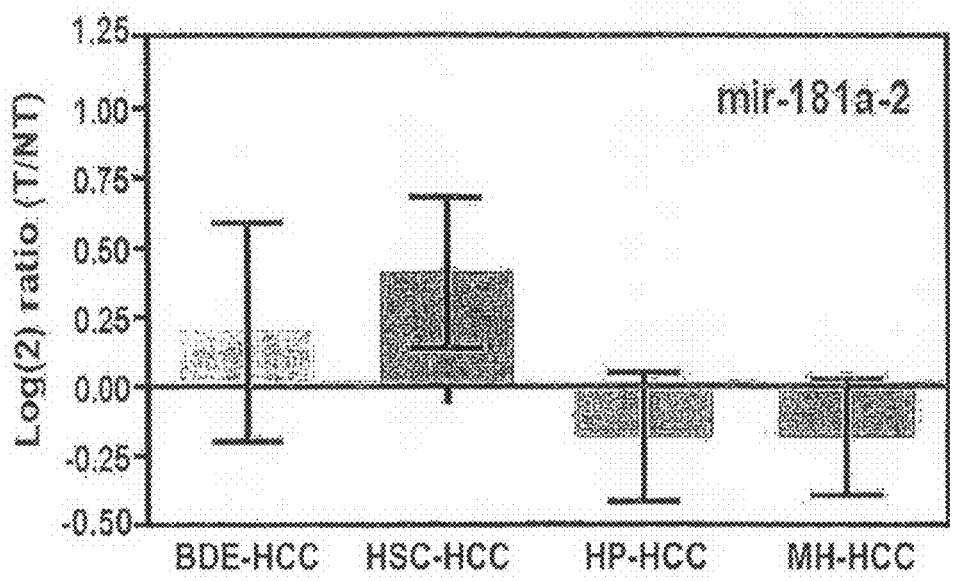
FIG. 1B shows the expression of mir-181a2 in log(2) ratio (of tumor to nontumor tissue) in HSC, DBE, HP, and MH-HCC cells based on microRNA analysis.
Figure 1E:
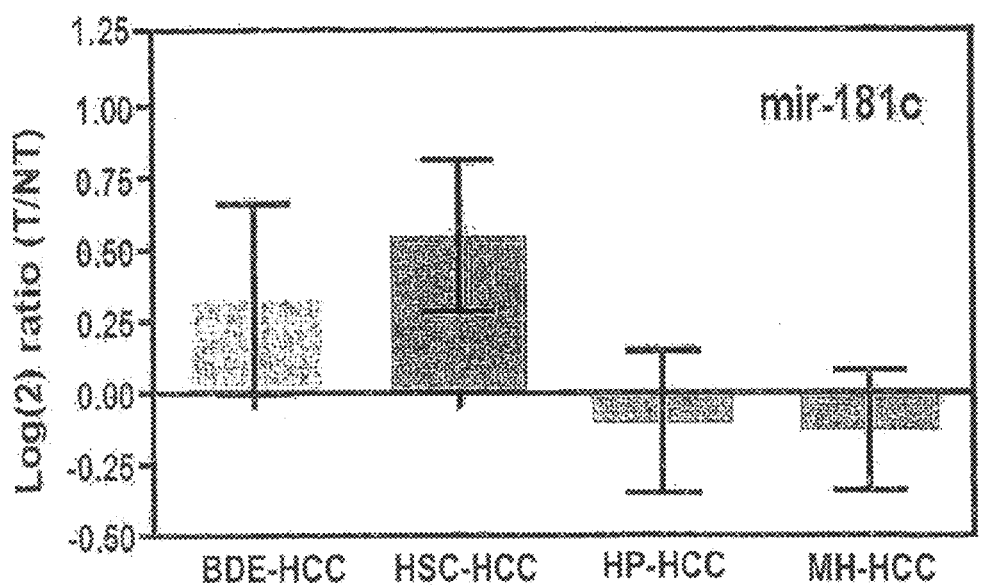
FIG. 1E shows the expression of mir-181c in log(2) ratio (of tumor to nontumor tissue) in HSC, DBE, HP, and MH-HCC cells based on microRNA analysis.
Figure 1F:
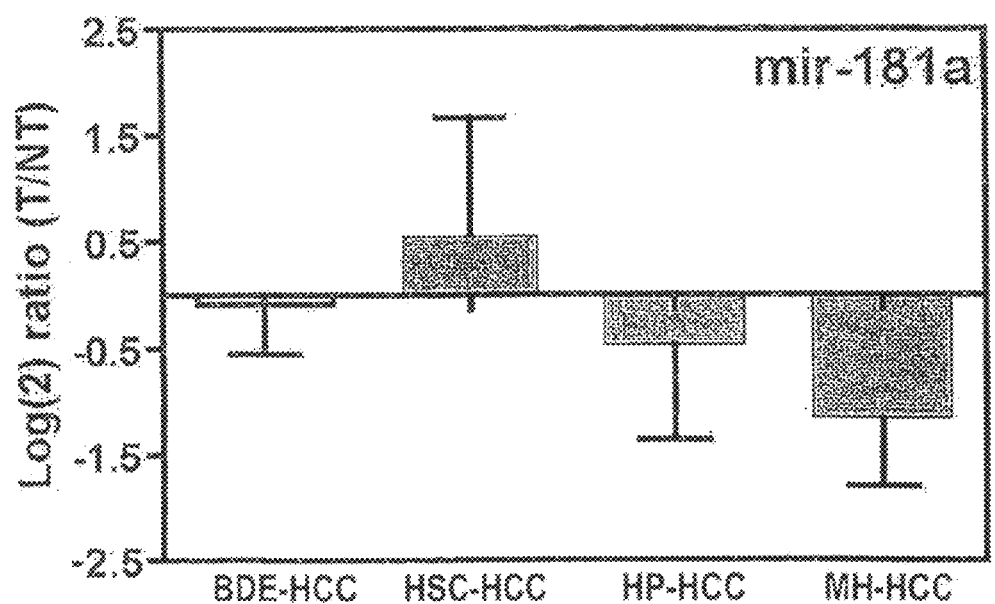
FIG. 1F shows the expression of mir-181a in log(2) ratio (of tumor to nontumor tissue) in HSC, DBE, HP, and MH-HCC cells as determined by RT-PCR.
Figure 1G:
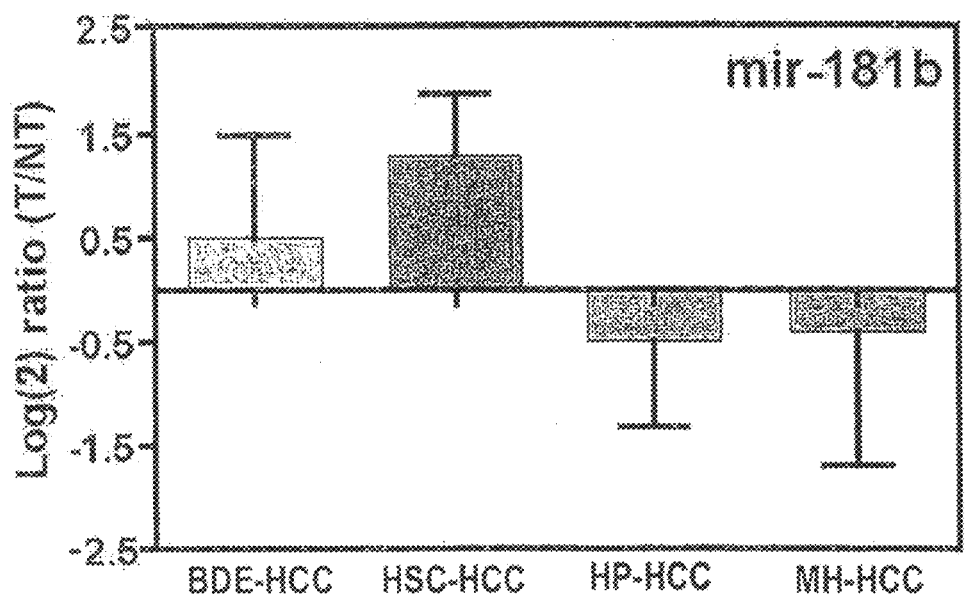
FIG. 1G shows the expression of mir-181b in log(2) ratio (of tumor to nontumor tissue) in HSC, DBE, HP, and MH-HCC cells as determined by RT-PCR.
Figure 1H:
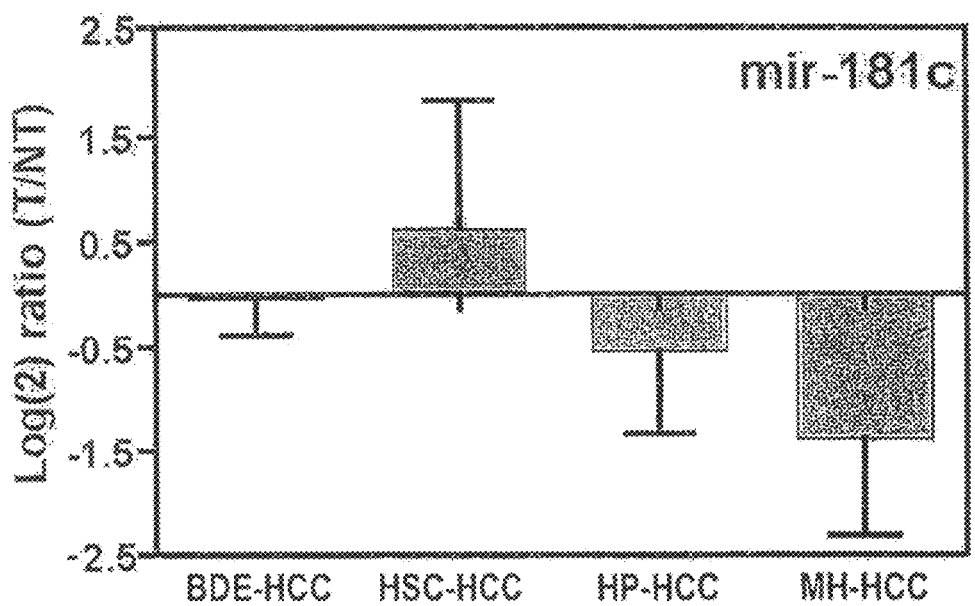
FIG. 1H shows the expression of mir-181c in log(2) ratio (of tumor to nontumor tissue) in HSC, DBE, HP, and MB-HCC cells as determined by RT-PCR.
Figure 1I:
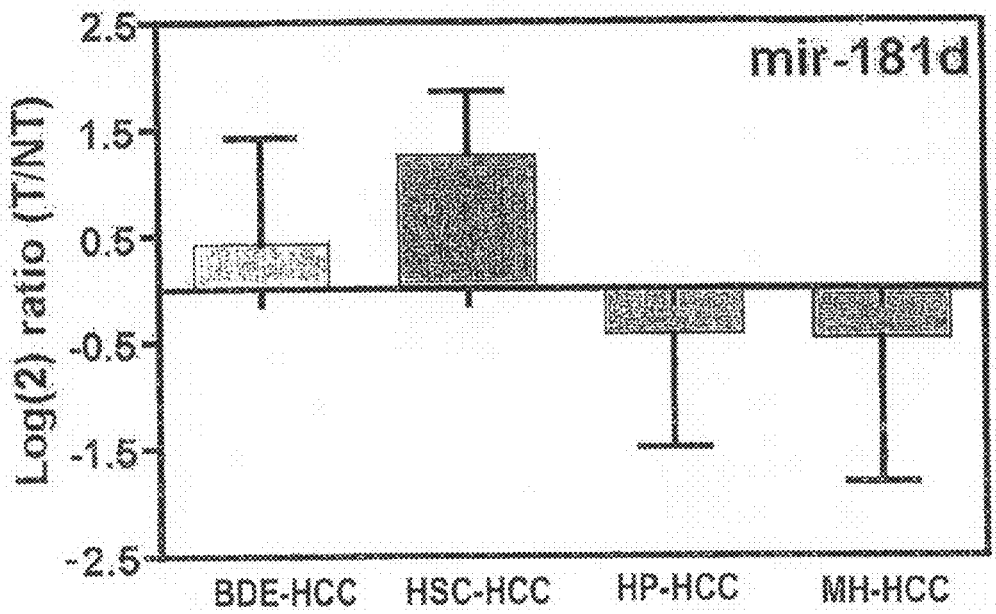
FIG. 1I shows the expression of mir-181d in log(2) ratio (of tumor to nontumor tissue) in HSC, DBE, HP, and MH-HCC cells as determined by RT-PCR.
Figure 1J:
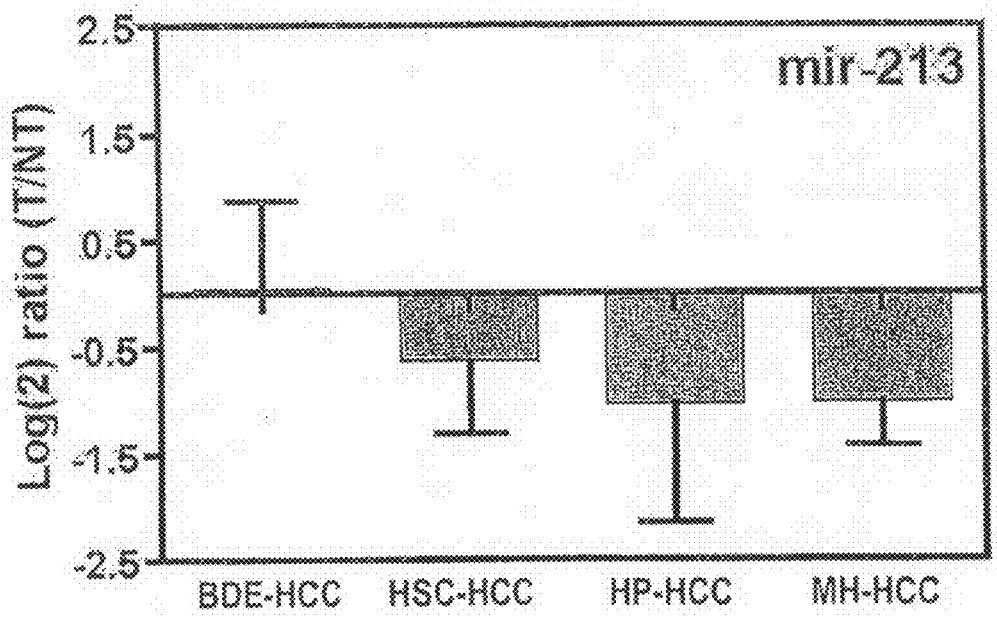
FIG. 1J shows the expression of mir-213 in log(2) ratio (of tumor to nontumor tissue) in HSC, DBE, HP, and MB-HCC cells as determined by RT-PCR.
Figure 2A:
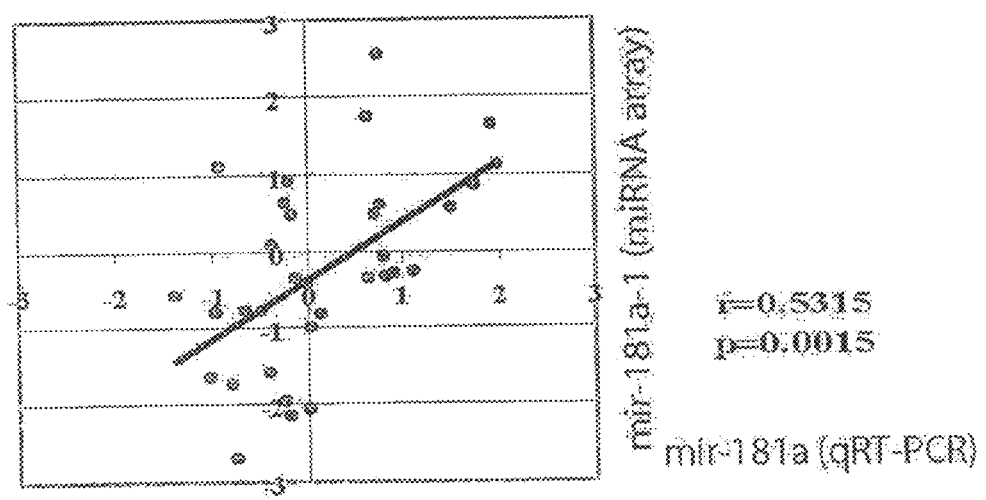
FIG. 2A shows a scatter plot of mir-181a1.
Figure 2B:
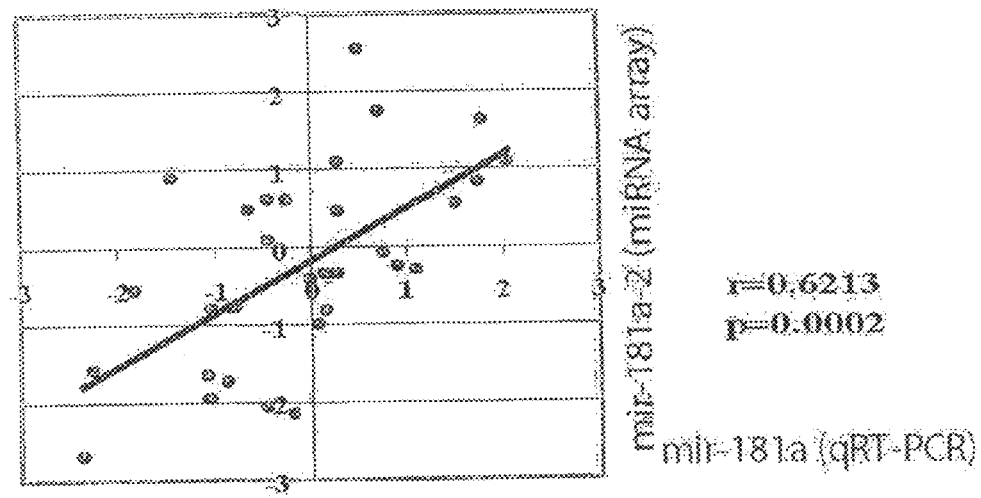
FIG. 2B shows a scatter plot of mir-181a2.
Figure 2C:
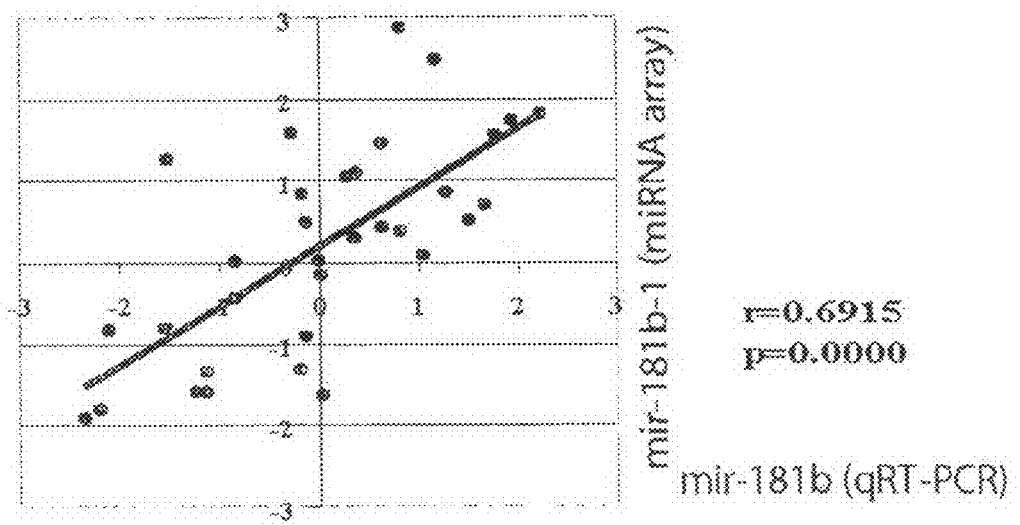
FIG. 2C shows a scatter plot of mir-181b1.
Figure 2D:
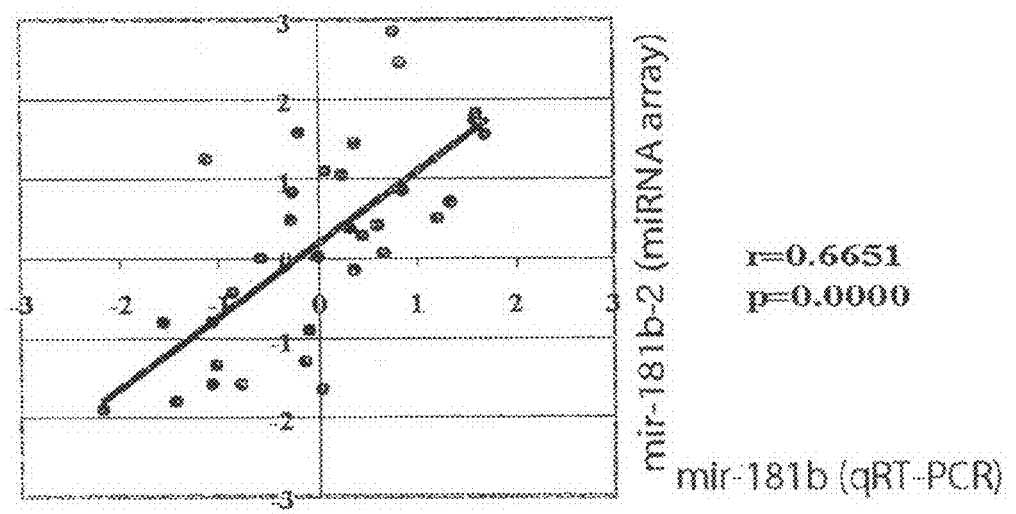
FIG. 2D shows a scatter plot of mir-181b2.
Figure 2E:
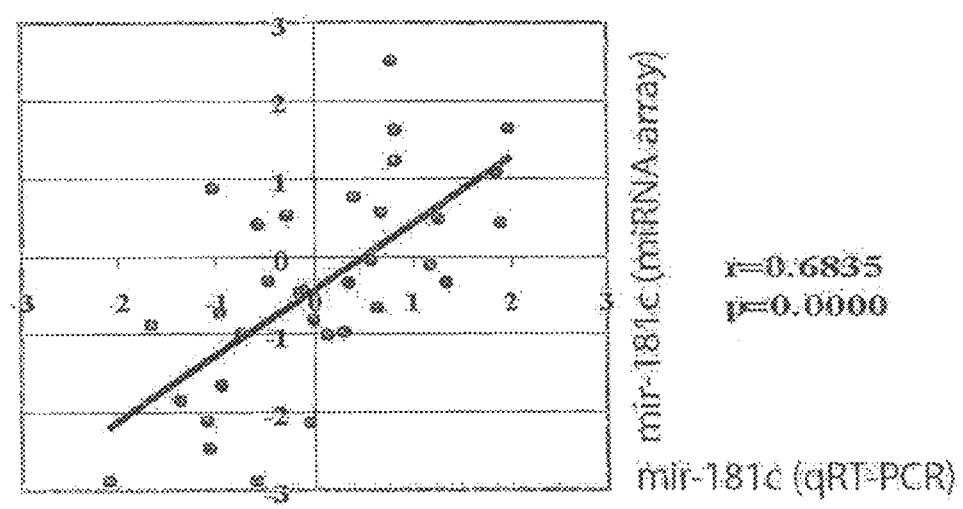
FIG. 2E shows a scatter plot of mir-181c.

Micro RNAs (or miRNAs) are small non-coding RNA gene products (e.g., ~22 nt) that exist in many organisms and play key regulatory roles in mRNA translation and degradation by base pairing to partially complementary sites of the mRNA, predominantly in the 3' untranslated region. Lee, *Science*, 294(5543):862-864 (2001); Lau, *Science*, 294(5543):858-862 (2001); Lagos, *Science*, 294(5543):853-858 (2001). miRNAs are expressed as long precursor RNAs that are processed by Drosha, a cellular nuclease, and subsequently transported to the cytoplasm by an Exportin-5-dependent mechanism. Yi, *Genes Dev,* 17(24):3011-3016 (2003); Gregory, *Cancer Res.,* 65(9):3509-3512 (2005). miRNAs are then cleaved by the DICER enzyme, resulting in approximately 17-24 nt miRNAs that associate with a RNA-induced silencing-like complex. Lee, *EMBO J,* 21(17):4663-4670 (2002); Hutvagner, *Science,* 297(5589):2056-2060 (2002).

The invention is predicated on the finding miRNA biomarkers are associated with HCC subtypes. For purposes of the invention, the HCC subtypes refer to hepatic stem cell-like HCC(HSC-HCC), which is epithelial cell adhesion molecule (EpCAM)+alpha-fetoprotein (AFP)+; bile duct epithelium-like HCC (BDE-HCC), which is EpCAM+AFP−; hepatocytic progenitor-like HCC (1-EP-HCC), which is EpCAM−AFP+; and mature hepatocyte-like HCC (MH-HCC), which is EpCAM−AFP−. The invention provides a set of biomarkers useful in identifying each HCC subtype.

In one embodiment, the invention provides a method of determining an HCC subtype in a subject comprising a) obtaining a sample from the subject, b) analyzing the sample for the expression of 1 or more biomarkers, and c) correlating the expression of the 1 or more biomarkers with the subtype of HCC in the subject. The expression of the biomarkers may be decreased or increased relative to normal control. The biomarkers are identified by SEQ ID NOs: 1-39 (see Table 1). In the inventive method, it is preferred that 2 or more, 5 or more, 10 or more, 15 or more, 20 or more, 25 or more, 30 or more, or 35 or more biomarkers are analyzed. More preferably, all 39 biomarkers are analyzed. For the determination of the HSC-HCC subtype, preferably at least the biomarkers identified by SEQ ID NOs: 1-19 are analyzed. For the determination of the BDE-HCC subtype, preferably at least the biomarkers identified by SEQ ID NOs: 2, 9-17, and 19-35 are analyzed. For the determination of the HP-HCC subtype, preferably at least the biomarkers identified by SEQ ID NOs: 1-8, 11-13, 17-18, 23, 28-29, and 33-39 are analyzed. For the determination of the MH-HCC subtype, preferably at least the biomarkers identified by SEQ ID NOs: 1, 8-12, 14-17, and 19-39 are analyzed.

In addition, it has been discovered that in contrast to mature liver cells, HCC stem cells are associated with (i.e., they express) the mir-181 family of miRNA biomarkers, particularly, mir-181a1, mir-181a2, mir-181b1, mir-181b2, and mir-181c, and that presence of HCC stem cells in a sample are indicative of the HSC-HCC subtype, which is associated with poor prognosis. Accordingly, in one embodiment, the invention provides a method of detecting the presence of HCC stem cells in a sample comprising a) obtaining a sample, b) assaying the sample to detect the presence of a mir-181 biomarker, and c) correlating the presence or absence of the mir-181 biomarker with the presence or absence of the HCC stem cell in the sample. For example, alternatively, EpCAM+AFP+ HCC stem cells may be detected by any suitable methods, e.g., immunofluorescence, immunohistochemistry, frozen activator cell sorting, side population methods, cell surface marker detection methods or in situ hybridization. For instance, in the side population technique, the cell-permeable DNA-binding dye Hoechst 33342 is loaded into the cell population of interest; stem cells and early progenitors subsequently pump this dye out via an ATP-binding cassette membrane pump-dependent mechanism, resulting in a low-fluorescence "tail" when the cells are analyzed by flow cytometry. In one embodiment, the method further comprises correlating the presence of the HCC stem cell in the sample with presence of HSC-HCC subtype in the sample. Advantageously, the detection of HCC stem cells in a sample may allow for earlier detection of the HSC-HCC subtype in a subject and thus lead to a greater likelihood of successful treatment and survival.

As used here, the term "biomarkers" is used interchangeably with "miRNA" and refers to those biomarkers associated with HCC, which include at least the 39 biomarkers in Table 1. In the inventive method, some (i.e., 1, 2, 3, 4, 5, 7, 7, 8, 9, 10, 15, 20, 25, 30, or 35) or all 39 of the biomarkers may be detected. Preferably, at least 2 or more, more preferably at least 5 or more biomarkers are detected. In embodiments where a mir-181 biomarker is detected, the biomarker may be one or more of mir-181a1, mir-181a2, mir-181b1, mir-181b2, and mir-181c, preferably. In this regard, some (i.e., 1, 2, 3, or 4) or all 5 of the mir-181 biomarkers are detected.

Suitable techniques for determining the presence and level of expression of the biomarkers in samples are within the skill in the art. According to one such method, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters by, e.g., the so-called "Northern" blotting technique. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are herein incorporated by reference. For example, the nucleic acid probe can be labeled with, e.g., a radionuclide such as $^3$H, $^{32}$P, $^{33}$P, $^{14}$C, or $^{35}$S; a heavy metal; or a ligand capable of functioning as a specific binding pair member for a labeled ligand (e.g., biotin, avidin or an antibody), a fluorescent molecule, a chemiluminescent molecule, an enzyme or the like.

Probes can be labeled to high specific activity by either the nick translation method of Rigby et al, *J. Mol. Biol.*, 113:237-251 (1977) or by the random priming method of Fienberg, *Anal. Biochem.*, 132:6-13 (1983), the entire disclosures of which are herein incorporated by reference. The latter can be a method for synthesizing $^{32}$P-labeled probes of high specific activity from RNA templates. For example, by replacing pre-existing nucleotides with highly radioactive nucleotides according to the nick translation method, it is possible to prepare $^{32}$P-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of biomarker levels. Using another approach, biomarker levels can be quantified by computerized imaging systems, such the Molecular Dynamics 400-B 2D Phosphorimager (Amersham Biosciences, Piscataway, N.J.).

Where radionuclide labeling of DNA or RNA probes is not practical, the random-primer method can be used to incorporate an analogue, for example, the dTTP analogue 5-(N-(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA blotting hybridization techniques, determining the levels of RNA expression can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference.

The relative number of mi-RNAs in a sample can also be determined by reverse transcription, followed by amplification of the reverse-transcribed transcripts by polymerase chain reaction (RT-PCR). The levels of RNA transcripts can be quantified in comparison with an internal standard, for example, the level of mRNA from a standard gene present in the same sample. A suitable gene for use as an internal standard includes, e.g., myosin or glyceraldehyde-3-phosphate dehydrogenase (G3PDH). The methods for quantitative RT-PCR and variations thereof are within the skill in the art.

In some instances, it may be desirable to simultaneously determine the expression level of a plurality of different biomarker genes in a sample. In certain instances, it may be desirable to determine the expression level of the transcripts of all known biomarker genes correlated with HCC. Assessing cancer-specific expression levels for hundreds of biomarker genes is time consuming and requires a large amount of total RNA (at least 20 μg for each Northern blot) and autoradiographic techniques that require radioactive isotopes. To overcome these limitations, an oligolibrary in microchip format may be constructed containing a set of probe oligonucleotides specific for a set of biomarker genes. For example, the oligolibrary may contain probes corresponding to all known biomarkers from the human genome. The microchip oligolibrary may be expanded to include additional miRNAs as they are discovered.

The microchip is prepared from gene-specific oligonucleotide probes generated from known miRNAs. For example, the array may contain two different oligonucleotide probes for each miRNA, one containing the active sequence and the other being specific for the precursor of the miRNA. The array may also contain controls such as one or more mouse sequences differing from human orthologs by only a few bases, which can serve as controls for hybridization stringency conditions. tRNAs from both species may also be printed on the microchip, providing an internal, relatively stable positive control for specific hybridization. One or more appropriate controls for non-specific hybridization may also be included on the microchip. For this purpose, sequences are selected based upon the absence of any homology with any known miRNAs.

The microchip may be fabricated by techniques known in the art. For example, probe oligonucleotides of an appropriate length, e.g., 20 nucleotides, are 5'-amine modified at position C6 and printed using suitable available microarray systems, e.g., the GENEMACHINE OmniGrid 100 Microarrayer and Amersham CODELINK activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g. 6 times SSPE/30% formamide at 25 degrees C. for 18 hours, followed by washing in 0.75 times TNT at 37 degrees C., for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary biomarker, in the subject sample. In an example, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding biomarker in the subject sample.

The use of the array has one or more advantages for miRNA expression detection. First, the global expression of several hundred genes can be identified in a same sample at one time point. Second, through careful design of the oligonucleotide probes, expression of both mature and precursor molecules can be identified. Third, in comparison with Northern blot analysis, the chip requires a small amount of RNA, and provides reproducible results using as low as 2.5 μg of total RNA. The relatively limited number of miRNAs (a few hundred per species) allows the construction of a common microarray for several species, with distinct oligonucleotide probes for each. Such a tool would allow for analysis of trans-species expression for each known biomarker under various conditions.

The subject may be a human or animal presenting with symptoms of HCC. Preferably, the subject is a human. The subject may or may not also have hepatitis B virus or cirrhosis (such as alcohol induced, primary biliary cirrhosis, genetic haemchromatosis, autoimmune hepatitis, primary sclerosing cholangitis). The HCC may be a solitary tumor, multinodular tumor, and/or a metastatic lesion.

The sample obtained from the subject may be liver tissue, which can be tumor tissue or normal tissue. Alternatively, the sample may be from the subject's serum or plasma, frozen biopsy tissue, paraffin embedded biopsy tissue, and combinations thereof.

The invention further provides a method for determining the prognosis of a subject by determining whether the subject has the HSC HCC, BDE-HCC, HP-HCC, or MH-HCC subtype. The inventive method of prognosis may be utilized in lieu of current methods of prognosis. Alternatively, the inventive method may be utilized in conjunction with conventional methods of prognosis. When a combined approach is utilized, the traditional prognostic approaches may include spiral computed tomography (CT) of the liver and thorax, magnetic resonance imaging (MRI) with contrast enhancement or angiography with lipiodol injection, and biopsy, as well as current staging systems.

The method further provides a treatment regimen that may be devised for the subject on the basis of the HCC subtype in the subject. In this regard, the inventive method allows for a more personalized approach to medicine as the aggressiveness of treatment may be tailored to the subtype of HCC in the subject.

In one embodiment, the invention takes advantage of the association between the biomarkers and the HCC subtypes. Accordingly, the invention provides methods of treatment comprising administering a therapeutically effective amount of a composition comprising a reagent comprising nucleic acid complementary to at least one of the biomarkers associated with HSC-HCC, BDE-HCC, HP-HCC, or MH-HCC.

In another embodiment, the invention takes advantage of the association between the mir-181 biomarkers and HCC stem cells in order to determine the HCC subtype in a subject and, optionally, correlate the HCC-subtype in the patient with a prognosis. The mir-181 biomarkers are associated with the hepatic stem cell-like (HSC) HCC subtype, which is EpCAM and AFP positive. EpCAM is a transmembrane protein containing three extracellular domains and one cytoplasmic domain. The function of EpCAM and the regulatory mechanism of its expression are largely unknown but are thought to involve cell-cell adhesion (Winter, *Exp. Cell. Res.*, 285(1): 50-58 (2003)). EpCAM and AFP are not expressed in mature liver tissue. The HSC HCC subtype typically has a poor prognosis and survival outcome (Lee, *Hepatology*, 40(3): 667-676 (2004); Lee, *Nat. Med.*, 12(4): 410-416 (2006)). Accordingly, the invention provides a method of determining whether the HCC detected is the HSC HCC subtype. The determination of the HCC subtype is particularly useful in determining the appropriate treatment for the subject, particularly because the EPCAM+AFP+HCC is associated with Wnt-β-catenin signaling. Wnt-β-catenin signaling is critical for maintaining the function of stem cells and abnormal activation has been linked to many human cancers, including HCC. The mir-181s can contribute Wnt-β-catenin signaling activation, possibly through Dickkoph-1 (i.e., DKK1) and nemo-like kinase (i.e., NLK), which are inhibitors of the Wnt-β-catenin pathway. The invention takes advantage of the regulatory link between mir-181s and HCC stem cells, and provides methods of prognosis, and treatment based thereon.

Treatment options may include traditional treatments as well as gene therapy approaches that specifically target the miRNAs described herein. Traditional treatment of HCC includes, for example, percutaneous ethanol injection (PEI), radiofrequency ablation, chemoembolisation, and chemotherapy. Treatment is determined based on the status of the subject and guidelines are known in the art. (See for example, Ryder, *Gut*, 52: 1-8 (2003)).

The invention further provides pharmaceutical compositions for use in the inventive treatment methods. In this regard, the invention provides a composition comprising a therapeutically effective amount of a reagent comprising a nucleic acid or nucleic acids complementary to at least one, preferably at least two of the biomarkers selected from those identified by SEQ ID NOs: 1-39 and a pharmaceutically acceptable carrier. Alternatively, the reagent may comprise nucleic acids complementary to at least 5 or more, 10 or more, 15 or more, 20 or more, 25 or more, 30 or more, or 35 or more of the biomarkers. The reagent may comprise only the nucleic acids or the nucleic acids in combination with delivery reagents such as recombinant plasmids, viral vectors, liposomes, etc. Preferably, for the treatment of HSC-HCC, the composition comprises nucleic acids complementary to the biomarkers identified by SEQ ID NOs: 1-19, even more preferably, the composition comprises nucleic acids complementary to mir-181a1, mir-181a2, mir-181b1, mir-181b2, and mir-181c, and a pharmaceutically acceptable carrier. Preferably, for the treatment of BDE-HCC, the composition comprises nucleic acids complementary to at least one, preferably at least 2 biomarkers identified by SEQ ID NOs: 2, 9-17, and 19-35, and a pharmaceutically acceptable carrier. Preferably, for the treatment of HP-HCC, the composition comprises nucleic acids complementary to at least one, preferably at least two biomarkers identified by SEQ ID NOs: 1-8, 11-13, 17-18, 23, 28, 29, and 33-39, and a pharmaceutically acceptable carrier. Preferably, for the treatment of MH-HCC, the composition comprises nucleic acids complementary to at least one, preferably to at least two biomarkers identified by SEQ ID NOs: 1, 8-12, 14-17, and 19-39, and a pharmaceutically acceptable carrier. The composition may bind and/or render ineffective (i.e., inhibit) the biomarkers, or alternatively, alter the expression of the gene coding for the biomarkers, thereby altering the amounts or levels of biomarkers produced, the technology for which are well known within the art.

In the practice of the present treatment methods, an effective amount of at least one composition which inhibits at least one of the biomarkers can also be administered to the subject. As used herein, "inhibiting" means that the biomarker levels and/or production of biomarker gene product from the corresponding gene in the cancer cell after treatment is less than the amount produced prior to treatment. In another embodiment, a composition that increases the expression of one or more of the biomarkers may be administered. One skilled in the art can readily determine whether biomarker levels or gene expression has been inhibited or increased in a cancer cell, using for example the techniques for determining biomarker transcript level discussed above.

As used herein, an "effective amount" of a composition that inhibits the biomarkers or biomarker gene expression is an amount sufficient to inhibit proliferation of a cancer cell in a subject suffering from HCC. One skilled in the art can readily determine an effective amount of an inhibiting composition to be administered to a given subject, by taking into account factors such as the size and weight of the subject; the extent of disease penetration; the age, health and sex of the subject; the route of administration; and whether the administration is regional or systemic.

For example, an effective amount of the expression-altering composition can be based on the approximate weight of a tumor mass to be treated. The approximate weight of a tumor mass can be determined by calculating the approximate volume of the mass, wherein one cubic centimeter of volume is roughly equivalent to one gram. Therefore, in one embodiment, an effective amount based on the weight of a tumor mass can utilized. Alternatively, an effective amount of the composition can be based on the approximate or estimated body weight of a subject to be treated. Preferably, such effective amounts are administered parenterally or enterally.

One skilled in the art can also readily determine an appropriate dosage regimen for administering a composition that alters biomarker levels or gene expression to a given subject. For example, the composition can be administered to the subject once (e.g. as a single injection or deposition). Alternatively, the composition can be administered once or twice daily to a subject for a period of from about three to about twenty-eight days, more preferably from about seven to about ten days. Alternatively, the composition may be administered once a day for seven days. Where a dosage regimen comprises multiple administrations, it is understood that the effective amount of the composition administered to the subject can comprise the total amount of composition administered over the entire dosage regimen.

Suitable compositions for inhibiting biomarker gene expression include double-stranded RNA (such as short- or small-interfering RNA or "siRNA"), antisense nucleic acids, and enzymatic RNA molecules such as ribozymes. Each of these compositions can be targeted to a given biomarker gene product and destroy or induce the destruction of the target biomarker gene product.

For example, expression of a given biomarker gene can be inhibited by inducing RNA interference of the biomarker gene with an isolated double-stranded RNA ("dsRNA") molecule which has at least 90%, for example 95%, 98%, 99% or 100%, sequence homology with at least a portion of the biomarker gene product. In a preferred embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target biomarker gene product.

As used herein, the siRNA is "substantially identical" to a target sequence contained within the target nucleic sequence, is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be an altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in one embodiment, the siRNA comprises at least one 3' overhang of from 1 to about 6 nucleotides (which includes ribonucleotides or deoxyribonucleotides) in length, preferably from 1 to about 5 nucleotides in length, more preferably from 1 to about 4 nucleotides in length, and particularly preferably from about 2 to about 4 nucleotides in length. In a preferred embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector for the isolated biomarker gene products. Exemplary methods for producing and testing dsRNA or siRNA molecules are described in U.S. Published Patent Application No. 2002/0173478 and U.S. Pat. No. 7,148,342, the entire disclosures of which are herein incorporated by reference.

Expression of a given biomarker gene can also be inhibited by an antisense nucleic acid. As used herein, an "antisense nucleic acid" refers to a nucleic acid molecule that binds to target RNA by means of RNA-RNA or RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, PNA) that generally comprise a nucleic acid sequence complementary to a contiguous nucleic acid sequence in a biomarker gene product. Preferably, the antisense nucleic acid comprises a nucleic acid sequence that is 50-100% complementary, more preferably 75-100% complementary, and most preferably 95-100% complementary to a contiguous nucleic acid sequence in an biomarker gene product.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators such as acridine or the inclusion of one or more nuclease-resistant group's.

Antisense nucleic acids can be produced chemically or biologically, or can be expressed from a recombinant plasmid or viral vector, as described above for the isolated biomarker gene products. Exemplary methods for producing and testing are within the skill in the art; see, e.g., Stein, *Science,* 261: 1004 (1993) and U.S. Pat. No. 5,849,902 to Woolf et al., the entire disclosures of which are herein incorporated by reference.

Expression of a given biomarker gene can also be inhibited by an enzymatic nucleic acid. As used herein, an "enzymatic nucleic acid" refers to a nucleic acid comprising a substrate binding region that has complementarity to a contiguous nucleic acid sequence of a biomarker gene product, and which is able to specifically cleave the biomarker gene product. Preferably, the enzymatic nucleic acid substrate binding region is 50-100% complementary, more preferably 75-100% complementary, and most preferably 95-100% complementary to a contiguous nucleic acid sequence in a biomarker gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated biomarker gene products. Exemplary methods for producing and testing dsRNA or siRNA molecules are described in Werner, *Nucl. Acids Res.,* 23:2092-96 (1995); Hammann, *Antisense and Nucleic Acid Drug Dev.,* 9:25-31 (1999); and U.S. Pat. No. 4,987,071, the entire disclosures of which are herein incorporated by reference.

Administration of at least one composition for inhibiting at least one biomarker or expression of a biomarker gene will inhibit the proliferation of cancer cells in a subject who has HCC. As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the inventive composition. An inhibition of cancer cell proliferation can also be inferred if the absolute number of such cells increases, but the rate of tumor growth decreases.

The number of cancer cells in a subject's body can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The inventive compositions can be administered to a subject by any method suitable for delivering these compositions to the cancer cells of the subject. For example, the compositions can be administered by methods suitable to transfect cells of the subject with these compositions. Preferably, the cells are transfected with a plasmid or viral vector comprising sequences encoding at least one biomarker gene product or biomarker gene expression inhibiting composition.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

For example, cells can be transfected with a liposomal transfer composition, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

The composition can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Preferred administration routes are injection, infusion and direct injection into the tumor.

In the present methods, the composition can be administered to the subject either as naked RNA, in combination with a delivery reagent, or as a nucleic acid (e.g., a recombinant plasmid or viral vector) comprising sequences that express the biomarker gene product or expression inhibiting composition. Suitable delivery reagents include, e.g., the Minis Transit TKO lipophilic reagent; lipofectin; lipofectamine; cellfectin; polycations (e.g., polylysine), and liposomes.

Recombinant plasmids and viral vectors comprising sequences that express the biomarker or biomarker gene expression inhibiting compositions, and techniques for delivering such plasmids and vectors to cancer cells, are discussed above.

In a preferred embodiment, liposomes are used to deliver a biomarker or biomarker gene expression-inhibiting composition (or nucleic acids comprising sequences encoding them) to a subject. Liposomes can also increase the blood half-life of the gene products or nucleic acids.

Liposomes suitable for use in the invention can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka, *Ann. Rev. Biophys. Bioeng.*, 9:467 (1980); and U.S. Pat. Nos. 4,235,871, 4,501,728, 4,837,028, and 5,019,369, the entire disclosures of which are herein incorporated by reference.

The liposomes for use in the present methods can comprise a ligand molecule that targets the liposome to cancer cells. Ligands which bind to receptors prevalent in cancer cells, such as monoclonal antibodies that bind to tumor cell antigens, are preferred.

The compositions of the present invention may include a pharmaceutically acceptable carrier. The term "pharmaceutically-acceptable carrier" as used herein means one or more compatible solid or liquid fillers, diluents, other excipients, or encapsulating substances which are suitable for administration into a human or veterinary patient. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner so as not to substantially impair the desired pharmaceutical efficacy. "Pharmaceutically acceptable" materials are capable of administration to a patient without the production of undesirable physiological effects such as nausea, dizziness, rash, or gastric upset. It is, for example, desirable for a therapeutic composition comprising pharmaceutically acceptable excipients not to be immunogenic when administered to a human patient for therapeutic purposes.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride, chlorobutanol, parabens and thimerosal.

The pharmaceutical compositions may conveniently be presented in unit dosage form and may be prepared by any of the methods well known in the art of pharmacy. All methods include the step of bringing the active agent into association with a carrier that constitutes one or more accessory ingredients. In general, the compositions are prepared by uniformly and intimately bringing the active composition into association with a liquid carrier, a finely divided solid carrier, or both, and then, if necessary, shaping the product.

Compositions suitable for parenteral administration conveniently comprise a sterile aqueous preparation of the inventive composition, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa. which is incorporated herein in its entirety by reference thereto.

The delivery systems of the invention are designed to include time-released, delayed release or sustained release delivery systems such that the delivering of the inventive composition occurs prior to, and with sufficient time, to cause sensitization of the site to be treated. The inventive composition may be used in conjunction with other therapeutic agents or therapies. Such systems can avoid repeated administrations of the inventive composition, increasing convenience to the subject and the physician, and may be particularly suitable for certain compositions of the present invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drags are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034 and 5,239, 660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

The invention further provides a method of assessing the efficacy of treatment of HCC in a subject by determining whether there are any remaining HCC stem cells remaining in the liver of the subject following a course of treatment. In this regard, a sample is obtained from the subject and assayed to detect the presence or absence of a mir-181 biomarker. The presence or absence of a mir-181 biomarker is then correlated with the presence or absence, respectively, of EpCAM+AFP+ HCC in a subject. This information is used to determine whether treatment of the HCC in the subject has or has not been effective.

The following examples further illustrate the invention but, of course, should not be construed as in any way limiting its scope.

EXAMPLES

The following techniques were utilized for the examples set forth below.

Clinical Specimens.

Hepatic tissues were obtained with informed consent from subjects who underwent radical resection between 2002 and 2003 at the Liver Cancer Institute and Zhongshan Hospital (Fudan University, Shanghai, China). The study was approved by the Institutional Review Board of the Liver Cancer Institute and National Institutes of Health. The sample enrollment criteria included those with a history of HBV infection or HBV-related liver cirrhosis, HCC diagnosed by two independent pathologists, detailed information on clinical presentation and pathological characteristics, as well as detailed follow-up data for at least 3 years, which included intrahepatic recurrence, intrahepatic venous metastasis, lymph node involvement, extrahepatic metastasis, disease-free, overall survival, and cause of death. The updated TNM classification is superior to other staging systems, including CLIP and OKUDA, for HCC subjects who undergo resection and was therefore chosen to stratify early stage subjects (TNM stage I and II) for analysis of miRNA prediction capacity. Varotti, *Eur J. Surg Oncol,* 31(7):760-767 (2005); Huang et al., *J. Gastroenterol Hepatol,* 20(5):765-771 (2005). A prospective study revealed that the BCLC system was superior to the new TNM classification system updated in 2002, therefore, Cox proportional hazards modeling based on early stage subjects categorized by BCLC (Stage 0 and A) was also performed. Gene expression profiles were conducted in primary HCC and corresponding noncancerous hepatic tissues from 244 Chinese HCC subjects. Among them, 93% had underlying cirrhosis and 68% had a serum alpha-fetoprotein (AFP) level>20 ng/mL. A total of 134 well-defined cases were used as the training group. Among them, 30 had primary HCC lesions accompanied by tumor emboli found in the major branches of the portal vein (n=25), inferior vena cava (n=2), or common bile duct (n=4; one also with tumor thrombi in inferior vena cava), and 104 had solitary HCC with no metastatis/recurrence found at follow-up (3 yr). In the validation analysis, a testing group of 110 independent cases was used whose prognosis could not be accurately determined at the time of resection by several HCC staging mechanisms. The testing cases included 43 multinodular and 67 solitary HCC. Of the 43 multinodular HCC cases, 18 developed intrahepatic recurrence and one developed extrahepatic metastatis in addition to an intrahepatic recurrence. Of the 67 solitary HCC cases, 4 subjects had a solitary tumor with an appearance of aggregated nodules, 10 developed intra- and/or extrahepatic metastasis while 49 developed intrahepatic recurrence confirmed at follow-up (3 yr). In addition, eight normal liver tissues from disease-free subjects (described in Budhu, *Cancer Cell,* 10(2):99-111 (2006)) were included as normal controls.

RNA Isolation and miRNA Arrays.

The RNA isolation and miRNA array methodology were carried out as described in Ye, *Nat Med,* 9(4):416-423 (2003); Cahn, *N Engl J. Med,* 353(17):1793-1802 (2005). In the analysis of the 244 HCC cases, RNA was isolated in a pair-wise fashion from tumor or non-tumor tissue and samples were selected in random order for miRNA analysis to avoid grouping bias. A total of 488 microarrays were performed. The microarray platform (V 2.0) was composed of 250 non-redundant human and 200 mouse miRNAs. To examine the robustness of the miRNA microarray platform, miRNA was analyzed to determine whether expression could differentiate 244 tissues from their paired surrounding noncancerous hepatic tissues. Using a supervised class comparison method with univariate paired t-test and a multivariate test with 1000 permutations of the class label with the false discovery rate set to $\leq 1$ with a 99% confidence, 209 non-redundant miR- NAs were identified that could significantly discriminate HCC tumor tissues (T) from their paired nontumor tissue (NT). These significant miRNAs clearly separated T and NT samples, illustrated by hierarchical clustering analysis. Multivariate class prediction algorithm analyses with 10% cross-validation and 100 random permutations indicated that these miRNAs can provide a statistically significant prediction of T and NT samples (p<0.01) with greater than 97% accuracy by the nearest neighbor predictor. These initial analyses indicated that the miRNA arrays were robust and could identify a significant difference between tumor and noncancerous hepatic tissue.

Statistical Analysis.

Unsupervised hierarchical clustering analysis was performed by the GENESIS software version 1.5 developed by Alexander Sturn (IBMT-TUG, Graz, Austria). The BRB ArrayTools Software V3.3 was used for supervised analysis as previously described (Ye, Nat Med, 9(4):416-423 (2003); Budhu, Cancer Cell, 10(2):99-111 (2006)). The Kaplan-Meier survival analysis was used to compare subject survival based on prediction results, using Excel-based WinSTAT software. The statistical p value was generated by the Cox-Mantel log-rank test. Cox proportional hazards regression was used to analyze the effect of sixteen clinical variables on subject survival or recurrence using STATA 9.2 (College Station, Tex.). The statistical significance was defined as p<0.05. TargetScan analysis was based on a website tool developed by Ben Lewis (Lewis, Cell, 120(1):15-20 (2005)). Cox proportional hazards regression was used to analyze the effect of clinical variables on subject overall and relapse-free survival, including age, sex, HBV active status, pre-resection AFP, cirrhosis, alanine transferase (ALT), Child-Pugh score, tumor size, tumor encapsulation, nodular type, status of microvascular invasion, Edmondson grade, and several HCC prognosis staging systems, including BCLC staging (Llovet, Semin Liver Dis, 19(3):329-338 (1999)); CLIP classification ("The Cancer of the Liver Italian Program", Hepatology, 28(3):751-755 (1998)), Okuda staging (Okuda, Cancer, 56(4):918-928 (1985)), and TNF classification (American Joint Committee on Cancer (AJCC)/International Union Against Cancer (UICC)'s TNM Classification of Malignant Tumours, 6th Edition, Hoboken, N.J., John Wiley & Sons 2002).

qRT-PCR.

Total RNA was extracted using TRIzol (Invitrogen, Carlsbad, Calif.). TACSTD1, BAMBI, DKK1, CCND1, CTNNB1, and MYC expression were measured in triplicate using Applied Biosystems 7700 Sequence Detection System (Foster City, Calif.). Probes used were: TACSTD1, Hs00158980_1; CTNNB1, HS00170025_1; BAMBI, HS00180818, DKK1, Hs00183740_1, CCND1, Hs00277039_1, CTNNB1, MYC, Hs00153408_1; 18S, Hs999999901_1 (Applied Biosystems). All procedures were performed according to manufacturer suggestion.

Immunohistochemical Analysis.

Immunohistochemical analysis was performed using Envision+ kits (DAKO USA, Carpinteria, Calif.) according to manufacturer instruction. Primary antibodies were used as follows: anti-β-catenin monoclonal antibody clone 14 (BD Transduction Laboratories, San Jose, Calif.) and anti-Ep-CAM monoclonal antibody clone VU-1D9 (Oncogene Research Products, San Diego, Calif.).

Immunofluorescence.

Cells were cultured on chamber slides and treated with indicated chemicals for 48 h. Cells were then fixed with 4% paraformaldehyde for 10 min, methanol for 20 min and incubated in phosphate-buffered saline. Samples were blocked with 10% normal donkey serum for 1 h at room temperature and stained with primary antibodies for 1 h at 37° C., followed by Alexa 568 Texas Red-conjugated anti-mouse antibodies (Molecular Probes, Eugene, Oreg.).

EMSA.

Recombinant Tcf-4 was expressed in E. coli as GST fusion protein and extracted. EMSA was performed using LightShift Chemiluminescent EMSA kit (Pierce, Rockford, Ill.) according to manufacturer instructions. Double-stranded DNA oligonucleotides containing the putative Tcf binding sites of EpCAM promoter and 10 adjacent nucleotides upstream and downstream were constructed and used as probes. Mutant TBE1 and TBE2 probes were also used.

Cell Lines, Antisense and Plasmids.

Known Hep3B type B, MHCC97 type C, Smmc7721 type D, HUH1 and HUH7 HCC cell lines were cultured routinely. Cells were transfected with pMSCV-mir-181b-1 for functional assays. HUH7 cells were also treated with 2'-O-methyl mir-181s antisense, an inhibitor of mir-181s.

Example 1

This example demonstrates that miRNA expression can differentiate HCC tissue from non-cancerous tissue and can distinguish among four subtypes of HCC.

Utilizing paired HCC tissue and surrounding non-HCC tissue samples from a total of 230 HCC patients, a total of 209 non-redundant miRNAs were found to provide 97% accuracy in correctly identifying the samples (multivariate p<0.01). Heterogeneity of the samples was evident and the samples were clustered based on the four HCC subtypes (HSC, BDE, HP, and MH).

Figure 10:
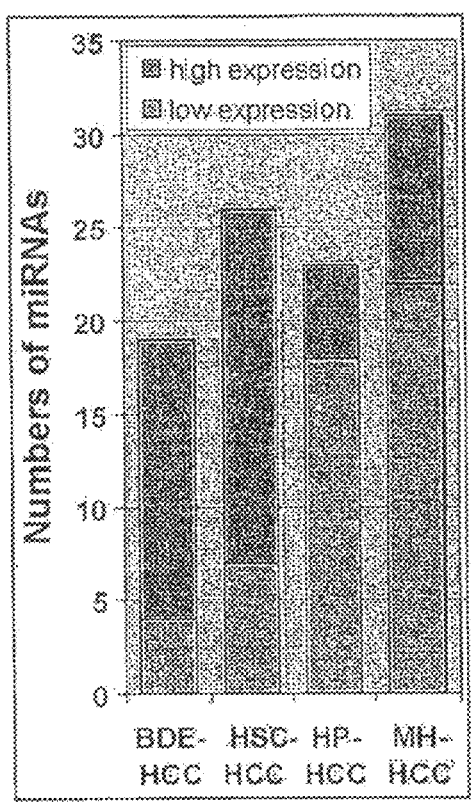
FIG. 10 is a graph of the number of miRNAs with increased and decreased expression in HSC-HCC, BDE-HCC, HP-HCC, and MH-HCC subtypes.

Expression of significant miRNAs among the four HCC subtypes were sought. Hierarchical clustering revealed that 39 pre-miRNA genes showed significant altered expression in the four HCC subtypes (p<0.002, FDR<0.05) from overlapping genes based on both class comparison and class prediction with a 10-fold cross validation to establish prediction accuracy (Table 1). Of the 39 miRNAs, some were up-regulated and others were down-regulated in each subtype (FIG. 10).

TABLE 1

| HCC Group | SEQ. ID No. | gene symbol | gene location | mature sequence | Parametric p-value | FDR | Permutation p-value |
|---|---|---|---|---|---|---|---|
| HSC | 1 | let-7a-1 | 9q22.32 | ugagguaguagguuguauagu | 0.0002 | 0.0089 | 0.0003 |
|  | 2 | let-7a-2 | 11q24.1 | ugagguaguagguuguauaguu | 0.0003 | 0.0101 | 0.0003 |
|  | 3 | let-7a-3 | 22q13.31 | ugagguaguagguuguaugguu | 0.0027 | 0.0362 | 0.0018 |
|  | 4 | let-7b | 22q13.31 | ugagguaguagguugugugguu | 0.0041 | 0.0455 | 0.0037 |
|  | 5 | let-7c | 21q21.1 | ugagguaguagguuguaugguu | 0.0019 | 0.0281 | 0.0013 |
|  | 6 | let-7d | 9q22.32 | agagguaguagguugcauagu | 0.0002 | 0.0087 | 0.0002 |
|  | 7 | let-7f-2 | Xp11.22 | ugagguaguagauuguauagu | 0.0028 | 0.0362 | 0.0026 |
|  | 8 | let-7g | 3p21.2 | ugagguaguaguuuguacagu | 0.0006 | 0.0138 | 0.0003 |
|  | 9 | mir-129-1 | 7q32.1 | cuuuugcggucugggcuugcu | 0.0004 | 0.0116 | 0.0003 |

TABLE 1-continued

|   |   |   |   |   |   |   |   |
|---|---|---|---|---|---|---|---|
|   | 10 | mir-129-2 | 11p11.2 | cuuuuugcggucugggcuugcu | 0.0002 | 0.0085 | 0.0001 |
|   | 11 | mir-181b-1 | 1q31.3 | aacauucauugcugucggugg | 0.0000 | 0.0001 | 0.0000 |
|   | 12 | mir-181b-2 | 9q33.3 | aacauucauugcugucggugg | 0.0000 | 0.0007 | 0.0000 |
|   | 13 | mir-196a-2 | 12q13.13 | uagguaguuucauguuguugg | 0.0036 | 0.0410 | 0.0045 |
|   | 14 | mir-337 | 14q32.31 | uccagcuccuauaugaugccuuu | 0.0001 | 0.0084 | 0.0001 |
|   | 15 | mir-93 | 7q22.1 | aaagugcuguucgugcagguag | 0.0025 | 0.0343 | 0.0023 |
|   | 16 | mir-17 | 13q31.3 | caaagugcuuacagugcagguagu | 0.0001 | 0.0079 | 0.0001 |
|   | 17 | mir-181c | 19p13.12 | aacauucaccugucggugagu | 0.0000 | 0.0011 | 0.0000 |
|   | 18 | mir-301 | 17q23.2 | cagugcaauaguauugucaaagc | 0.0044 | 0.0473 | 0.0040 |
|   | 19 | mir-92-2 | Xq26.2 | uauugcacuugucccggccug | 0.0003 | 0.0101 | 0.0002 |
| BDE | 20 | mir-106a | Xq26.2 | aaaagugcuuacagugcagguagc | 0.0002 | 0.0085 | 0.0001 |
|   | 21 | mir-106b | 7q22.1 | uaaagugcugacagugcagau | 0.0006 | 0.0135 | 0.0006 |
|   | 9 | mir-129-1 | 7q32.1 | cuuuuugcggucugggcuugcu | 0.0004 | 0.0116 | 0.0003 |
|   | 16 | mir-17 | 13q31.3 | caaagugcuuauagugcagguagu | 0.0001 | 0.0079 | 0.0001 |
|   | 22 | mir-181a-1 | 1q31.3 | aacuucaacgcugucggugagu | 0.0004 | 0.0108 | 0.0003 |
|   | 23 | mir-181a-2 | 9q33.3 | aacauucaacgcugucggugagu | 0.0000 | 0.0039 | 0.0000 |
|   | 11 | mir-181b-1 | 1q31.3 | aacauucauugcugucggugg | 0.0000 | 0.0001 | 0.0000 |
|   | 12 | mir-181b-2 | 9q33.3 | aacauucauugcugucggugg | 0.0000 | 0.0007 | 0.0000 |
|   | 17 | mir-181c | 19p13.12 | aacauucaaccugucggugagu | 0.0000 | 0.0011 | 0.0000 |
|   | 24 | mir-20a | 13q31.3 | uaaagugcuuauagugcagguag | 0.0005 | 0.0123 | 0.0007 |
|   | 25 | mir-221 | Xp11.3 | agcuacauugucucugcuggguuu | 0.0002 | 0.0085 | 0.0004 |
|   | 26 | mir-222 | Xp11.3 | agcaucucuggcuacugggucuc | 0.0006 | 0.0135 | 0.0004 |
|   | 27 | mir-25 | 7q22.1 | cauugcacuugucucggcuga | 0.0000 | 0.0039 | 0.0000 |
|   | 28 | mir-32 | 9q31.3 | uauugcacauuacuaaguugc | 0.0000 | 0.0007 | 0.0000 |
|   | 29 | mir-323 | 14q32.31 | gcacauuacacggucgaccucu | 0.0001 | 0.0079 | 0.0001 |
|   | 14 | mir-337 | 14q32.31 | uccagcuccuauaugaugccuuu | 0.0001 | 0.0084 | 0.0001 |
|   | 30 | mir-92-1 | 13q31.3 | uauugcacuugucccggccug | 0.0014 | 0.0218 | 0.0012 |
|   | 19 | mir-92-2 | Xq26.2 | uauugcacuugucccggccug | 0.0003 | 0.0101 | 0.0002 |
|   | 15 | mir-93 | 7q22.1 | aaagugcuguucgugcagguag | 0.0025 | 0.0343 | 0.0023 |
|   | 2 | let-7a-2 | 11q24.1 | ugagguaguagguuguauaguu | 0.0003 | 0.0101 | 0.0003 |
|   | 31 | mir-122a | 18q21.31 | uggagugugacaaugguguuugu | 0.0032 | 0.0391 | 0.0049 |
|   | 32 | mir-125b-1 | 11q24.1 | ucccugagacccuaacuuguga | 0.0007 | 0.0138 | 0.0003 |
|   | 33 | mir-125b-2 | 21q21.1 | ucccugagacccuaacuuguga | 0.0007 | 0.0145 | 0.0009 |
|   | 10 | mir-129-2 | 11p11.2 | cuuuuagcggucugggcuugcu | 0.0002 | 0.0085 | 0.0001 |
|   | 34 | mir-29a | 7q32.3 | uagcaccaucugaaaucgguu | 0.0002 | 0.0085 | 0.0004 |
|   | 35 | mir-29b-2 | 1q32.2 | uagcaccauuugaaaucaguguu | 0.0004 | 0.0116 | 0.0009 |
| HP | 28 | mir-32 | 9q31.3 | uauugcacauuacuaaguugc | 0.0000 | 0.0007 | 0.0000 |
|   | 29 | mir-323 | 14q32.31 | gcacauuacacggucgaccucu | 0.0001 | 0.0079 | 0.0001 |
|   | 18 | mir-301 | 17q23.2 | cagugcaauaguauugucaaagc | 0.0044 | 0.0473 | 0.0040 |
|   | 36 | mir-324 | 17p13.1 | cgcaucccuagggcauuggugu | 0.0038 | 0.0418 | 0.0035 |
|   | 37 | mir-99b | 19q13.41 | cacccguagaaccgaccuugcg | 0.0036 | 0.0410 | 0.0034 |
|   | 1 | let-7a-1 | 9q22.32 | ugagguaguagguuguauagu | 0.0002 | 0.0089 | 0.0003 |
|   | 2 | let-7a-2 | 11q24.1 | ugagguaguagguuguauaguu | 0.0003 | 0.0101 | 0.0003 |
|   | 3 | let-7a-3 | 22q13.31 | ugagguaguagguuguauagu | 0.0027 | 0.0362 | 0.0018 |
|   | 4 | let-7b | 22q13.31 | ugagguaguagguuguguggu | 0.0041 | 0.0455 | 0.0037 |
|   | 5 | let-7c | 21q21.1 | ugagguaguagguuguauggu | 0.0019 | 0.0281 | 0.0013 |
|   | 6 | let-7d | 9q22.32 | agagguaguagguugcauagu | 0.0002 | 0.0087 | 0.0002 |
|   | 7 | let-7f-2 | Xp11.22 | ugagguaguagauuguauagu | 0.0028 | 0.0362 | 0.0026 |
|   | 8 | let-7g | 3p21.2 | ugagguaguaguuuguacagu | 0.0006 | 0.0138 | 0.0003 |
|   | 33 | mir-125b-2 | 21q23.1 | ucccugagacccuaacuuguga | 0.0007 | 0.0145 | 0.0009 |
|   | 23 | mir-181a-2 | 9q33.3 | aacauucaacgcugucggugagu | 0.0000 | 0.0039 | 0.0000 |
|   | 11 | mir-181b-1 | 1q31.3 | aacauucauugcugucggugg | 0.0000 | 0.0001 | 0.0000 |
|   | 12 | mir-181b-2 | 9q33.3 | aacauucauugcugucggugg | 0.0000 | 0.0007 | 0.0000 |
|   | 17 | mir-181c | 19p13.12 | aacauucaaccugucggugagu | 0.0000 | 0.0011 | 0.0000 |
|   | 13 | mir-196a-2 | 12q13.13 | uagguaguuucauguuguugg | 0.0036 | 0.0410 | 0.0045 |
|   | 34 | mir-29a | 7q32.3 | uagcaccaucugaaaucgguu | 0.0002 | 0.0085 | 0.0004 |
|   | 38 | mir-29b-1 | 7q32.3 | uagcaccauuugaaaucaguguu | 0.0008 | 0.0166 | 0.0022 |
|   | 35 | mir-29b-2 | 1q32.2 | uagcaccauuugaaaucaguguu | 0.0004 | 0.0116 | 0.0009 |
|   | 39 | mir-29c | 1q32.2 | uagcaccauuugaaaucggu | 0.0015 | 0.0232 | 0.0020 |
| MH | 1 | let-7a-1 | 9q22.32 | ugagguaguagguuguauagu | 0.0002 | 0.0089 | 0.0003 |
|   | 31 | mir-122a | 18q21.31 | uggagugugacaaugguguuugu | 0.0032 | 0.0391 | 0.0049 |
|   | 32 | mir-125b-1 | 11q24.1 | ucccugagacccuaacuuguga | 0.0007 | 0.0138 | 0.0003 |
|   | 33 | mir-125b-2 | 21q21.1 | ucccugagacccuaacuuguga | 0.0007 | 0.0145 | 0.0009 |
|   | 10 | mir-129-2 | 11p11.2 | cuuuuugcggucugggcuugcu | 0.0002 | 0.0085 | 0.0001 |
|   | 34 | mir-29a | 7q32.3 | uagcaccaucugaaaucgguu | 0.0002 | 0.0085 | 0.0004 |
|   | 38 | mir-29b-1 | 7q32.3 | uagcaccauuugaaaucaguguu | 0.0008 | 0.0166 | 0.0022 |
|   | 35 | mir-29b-2 | 1q32.2 | uagcaccauuugaaaucaguguu | 0.0004 | 0.0116 | 0.0009 |
|   | 39 | mir-29c | 1q32.2 | uagcaccauuugaaaucggu | 0.0015 | 0.0232 | 0.0020 |
|   | 8 | let-7g | 3p21.2 | ugagguaguaguuuguacagu | 0.0006 | 0.0138 | 0.0003 |
|   | 20 | mir-106a | Xq26.2 | aaaagugcuuacagugcagguagc | 0.0002 | 0.0085 | 0.0001 |
|   | 21 | mir-106b | 7q22.1 | uaaagugcugacagugcagau | 0.0006 | 0.0135 | 0.0006 |
|   | 9 | mir-129-1 | 7q32.1 | cuuuuugcggucugcgcuugcu | 0.0004 | 0.0116 | 0.0003 |
|   | 16 | mir-17 | 13q31.3 | caaagugcuuacagugcagguagu | 0.0001 | 0.0079 | 0.0001 |
|   | 22 | mir-181a-1 | 1q31.3 | aacauucaacgcugucggugagu | 0.0004 | 0.0108 | 0.0003 |
|   | 23 | mir-181a-2 | 9q33.3 | aacauucaacgcugucggugagu | 0.0000 | 0.0039 | 0.0000 |
|   | 11 | mir-181b-1 | 1q31.3 | aacauucauugcugucggugg | 0.0000 | 0.0001 | 0.0000 |
|   | 12 | mir-181b-2 | 9q33.3 | aacauucauugcugucggugg | 0.0000 | 0.0007 | 0.0000 |

TABLE 1-continued

| | | | | | | |
|---|---|---|---|---|---|---|
| 17 | mir-181c | 19p13.12 | aacauucaaccugucggugagu | 0.0000 | 0.0011 | 0.0000 |
| 24 | mir-20a | 13q31.3 | uaaagugcuuauagugcagguag | 0.0005 | 0.0123 | 0.0007 |
| 25 | mir-221 | Xp11.3 | agcuacauugucugcugguuu | 0.0002 | 0.0085 | 0.0004 |
| 26 | mir-222 | Xp11.3 | agcuacaucuggcuacuaggucuc | 0.0006 | 0.0135 | 0.0004 |
| 27 | mir-25 | 7q22.1 | cauugcacagugucucggucuga | 0.0000 | 0.0039 | 0.0000 |
| 28 | mir-32 | 9q31.3 | uauugcacauuacuaaguugc | 0.0000 | 0.0007 | 0.0000 |
| 29 | mir-323 | 14q32.31 | gcacauuacacggucgaccucu | 0.0001 | 0.0079 | 0.0001 |
| 36 | mir-324 | 17p13.1 | cgcauccccuagggcauuggugu | 0.0038 | 0.0418 | 0.0035 |
| 14 | mir-337 | 14q32.31 | uccagcuccuauaugaugccuuu | 0.0001 | 0.0084 | 0.0001 |
| 30 | mir-92-1 | 13q31.3 | uauugcacuugucccggccug | 0.0014 | 0.0218 | 0.0012 |
| 19 | mir-92-2 | Xq26.2 | uauugcacuugucccggccug | 0.0003 | 0.0101 | 0.0002 |
| 15 | mir-93 | 7q22.1 | aaagugcuguucgugcagguag | 0.0025 | 0.0343 | 0.0023 |
| 37 | mir-99b | 19q13.41 | cacccguagaaccgaccuugcg | 0.0036 | 0.0410 | 0.0034 |

| HCC Group | SEQ. ID No. | Geom mean of intensities HCC | | | | Normal | Non-HCC | | | | up/down |
|---|---|---|---|---|---|---|---|---|---|---|---|
| | | BDE | HSC | HPC | MH | Liver | BDE | HSC | HPC | MH | |
| HSC | 1 | 720 | 491 | 442 | 592 | 720 | 4030 | 2910 | 2282 | 2409 | up |
| | 2 | 1592 | 1035 | 878 | 1136 | 1570 | 191 | 194 | 203 | 192 | up |
| | 3 | 1406 | 996 | 999 | 1185 | 1450 | 1246 | 1386 | 1474 | 1317 | up |
| | 4 | 2134 | 1675 | 1529 | 1826 | 2202 | 147 | 180 | 119 | 128 | up |
| | 5 | 1614 | 1226 | 1048 | 1353 | 2017 | 1048 | 1055 | 1159 | 980 | up |
| | 6 | 893 | 632 | 556 | 670 | 976 | 1191 | 1071 | 1011 | 934 | up |
| | 7 | 482 | 345 | 326 | 422 | 478 | 733 | 661 | 692 | 661 | up |
| | 8 | 1043 | 766 | 658 | 801 | 962 | 2050 | 1419 | 1441 | 1363 | up |
| | 9 | 274 | 265 | 215 | 170 | 178 | 3002 | 3067 | 2779 | 2859 | up |
| | 10 | 484 | 338 | 404 | 446 | 608 | 2199 | 2007 | 2127 | 1989 | up |
| | 11 | 1182 | 1344 | 926 | 719 | 608 | 615 | 525 | 513 | 509 | up |
| | 12 | 1298 | 1613 | 1153 | 988 | 864 | 1434 | 1431 | 1332 | 1294 | up |
| | 13 | 2465 | 1585 | 1226 | 1533 | 1791 | 2477 | 2742 | 2470 | 2432 | up |
| | 14 | 217 | 204 | 168 | 89 | 215 | 1080 | 1029 | 1023 | 1013 | up |
| | 15 | 1973 | 1950 | 1589 | 1273 | 901 | 2303 | 2082 | 1983 | 1947 | up |
| | 16 | 1608 | 2957 | 1994 | 1650 | 1376 | 1972 | 2305 | 2050 | 2171 | down |
| | 17 | 564 | 886 | 561 | 537 | 515 | 584 | 739 | 763 | 741 | down |
| | 18 | 6047 | 11619 | 14523 | 13198 | 25310 | 13590 | 16251 | 15375 | 14177 | down |
| | 19 | 10397 | 19133 | 14127 | 11409 | 18228 | 7590 | 13765 | 15979 | 15213 | down |
| BDE | 20 | 1471 | 2316 | 1733 | 1318 | 1239 | 1848 | 1767 | 1727 | 1699 | up |
| | 21 | 860 | 1078 | 860 | 712 | 520 | | | | | up |
| | 9 | 274 | 265 | 215 | 170 | 178 | 191 | 194 | 203 | 192 | up |
| | 16 | 1608 | 2957 | 1994 | 1650 | 1376 | 1972 | 2305 | 2050 | 2171 | up |
| | 22 | 1081 | 1355 | 991 | 921 | 804 | 1024 | 1137 | 1132 | 1098 | up |
| | 23 | 639 | 858 | 588 | 526 | 499 | 719 | 767 | 815 | 768 | up |
| | 11 | 1182 | 1344 | 926 | 719 | 608 | 1048 | 1055 | 1159 | 980 | up |
| | 12 | 1298 | 1613 | 1153 | 988 | 864 | 1246 | 1386 | 1474 | 1317 | up |
| | 17 | 564 | 886 | 561 | 537 | 515 | 584 | 739 | 763 | 741 | up |
| | 24 | 1201 | 1842 | 1376 | 1042 | 718 | | | | | up |
| | 25 | 2023 | 3332 | 2103 | 1956 | 678 | 891 | 1121 | 1219 | 1160 | up |
| | 26 | 1573 | 1920 | 1492 | 1237 | 640 | 761 | 769 | 968 | 846 | up |
| | 27 | 2713 | 3722 | 2714 | 2141 | 3056 | | | | | up |
| | 28 | 1140 | 1536 | 1227 | 800 | 1296 | 1366 | 1242 | 1219 | 1060 | up |
| | 29 | 200 | 213 | 203 | 83 | | | | | | up |
| | 14 | 217 | 204 | 168 | 89 | 215 | 147 | 180 | 119 | 128 | up |
| | 30 | 17617 | 25783 | 21298 | 17127 | 21489 | 24398 | 24972 | 24312 | 22036 | up |
| | 19 | 10397 | 19133 | 14127 | 11409 | 18228 | 13590 | 16251 | 15375 | 14177 | up |
| | 15 | 1973 | 1950 | 1589 | 1273 | 901 | 2050 | 1419 | 1441 | 1363 | up |
| | 2 | 1592 | 1035 | 878 | 1136 | 1570 | 2303 | 2082 | 1983 | 1947 | down |
| | 31 | 687 | 529 | 651 | 848 | 1338 | 1730 | 1609 | 1491 | 1625 | down |
| | 32 | 1467 | 905 | 923 | 1510 | 3329 | 4016 | 3551 | 3319 | 3336 | down |
| | 33 | 1696 | 1154 | 1202 | 1801 | 3245 | 3608 | 3620 | 3529 | 3471 | down |
| | 10 | 484 | 338 | 404 | 446 | 608 | 615 | 525 | 513 | 509 | down |
| | 34 | 1477 | 1030 | 964 | 1630 | 1150 | 2289 | 2304 | 2036 | 2166 | down |
| | 35 | 1076 | 984 | 926 | 1510 | 1234 | 1690 | 2229 | 2032 | 2034 | down |
| HP | 28 | 1140 | 1536 | 1227 | 800 | 1296 | 1366 | 1242 | 1219 | 1060 | up |
| | 29 | 200 | 213 | 203 | 83 | | | | | | up |
| | 18 | 6047 | 11619 | 14523 | 13198 | 25310 | 7590 | 13765 | 15979 | 15213 | up |
| | 36 | 413 | 432 | 434 | 359 | 415 | 379 | 384 | 405 | 403 | up |
| | 37 | 239 | 248 | 257 | 200 | 165 | 200 | 179 | 202 | 190 | up |
| | 1 | 720 | 491 | 442 | 592 | 720 | 1191 | 1071 | 1011 | 934 | down |
| | 2 | 1592 | 1035 | 878 | 1136 | 1570 | 2303 | 2082 | 1983 | 1947 | down |
| | 3 | 1406 | 996 | 999 | 1185 | 1450 | 2199 | 2007 | 2127 | 1989 | down |
| | 4 | 2134 | 1675 | 1529 | 1826 | 2202 | 3002 | 3067 | 2779 | 2859 | down |
| | 5 | 1614 | 1226 | 1048 | 1353 | 2017 | 2477 | 2742 | 2470 | 2432 | down |
| | 6 | 893 | 632 | 556 | 670 | 976 | 1080 | 1029 | 1023 | 1013 | down |
| | 7 | 482 | 345 | 326 | 422 | 478 | 733 | 661 | 692 | 661 | down |
| | 8 | 1043 | 766 | 658 | 801 | 962 | 1434 | 1431 | 1332 | 1294 | down |
| | 33 | 1696 | 1154 | 1202 | 1801 | 3245 | 3608 | 3620 | 3529 | 3471 | down |

TABLE 1-continued

|    |    |      |      |      |      |      |       |       |       |       |      |
|----|----|------|------|------|------|------|-------|-------|-------|-------|------|
|    | 23 |  639 |  858 |  588 |  526 |  499 |   719 |   767 |   815 |   768 | down |
|    | 11 | 1182 | 1344 |  926 |  719 |  608 |  1048 |  1055 |  1159 |   980 | down |
|    | 12 | 1298 | 1613 | 1153 |  988 |  864 |  1246 |  1386 |  1474 |  1317 | down |
|    | 17 |  564 |  886 |  561 |  537 |  515 |   584 |   739 |   763 |   741 | down |
|    | 13 | 2465 | 1585 | 1226 | 1533 | 1791 |  4030 |  2910 |  2282 |  2409 | down |
|    | 34 | 1477 | 1030 |  964 | 1630 | 1150 |  2289 |  2304 |  2036 |  2166 | down |
|    | 38 | 1194 |  904 |  749 | 1308 |  918 |  1866 |  2062 |  1751 |  1813 | down |
|    | 35 | 1076 |  984 |  926 | 1510 | 1234 |  1690 |  2229 |  2032 |  2034 | down |
|    | 39 | 1047 |  917 |  820 | 1308 | 1018 |  1619 |  2165 |  1895 |  1797 | down |
| MH |  1 |  720 |  491 |  442 |  592 |  720 |   615 |   525 |   513 |   509 | up   |
|    | 31 |  687 |  529 |  651 |  848 | 1338 |  1191 |  1071 |  1011 |   934 | up   |
|    | 32 | 1467 |  905 |  923 | 1510 | 3329 |  1730 |  1609 |  1491 |  1625 | up   |
|    | 33 | 1696 | 1154 | 1202 | 1801 | 3245 |  4016 |  3551 |  3319 |  3336 | up   |
|    | 10 |  484 |  338 |  404 |  446 |  608 |  3608 |  3620 |  3529 |  3471 | up   |
|    | 34 | 1477 | 1030 |  964 | 1630 | 1150 |  2289 |  2304 |  2036 |  2166 | up   |
|    | 38 | 1194 |  904 |  749 | 1308 |  918 |  1866 |  2062 |  1751 |  1813 | up   |
|    | 35 | 1076 |  984 |  926 | 1510 | 1234 |  1690 |  2229 |  2032 |  2034 | up   |
|    | 39 | 1047 |  917 |  820 | 1308 | 1018 |  1619 |  2165 |  1895 |  1797 | up   |
|    |  8 | 1043 |  766 |  658 |  801 |  962 |  1434 |  1431 |  1332 |  1294 | down |
|    | 20 | 1471 | 2316 | 1733 | 1318 | 1239 |   719 |   767 |   815 |   768 | down |
|    | 21 |  860 | 1078 |  860 |  712 |  520 |  1048 |  1055 |  1159 |   980 | down |
|    |  9 |  274 |  265 |  215 |  170 |  178 |  1246 |  1386 |  1474 |  1317 | down |
|    | 16 | 1608 | 2957 | 1994 | 1650 | 1376 |  1972 |  2305 |  2050 |  2171 | down |
|    | 22 | 1081 | 1355 |  991 |  921 |  804 |  1024 |  1137 |  1132 |  1098 | down |
|    | 23 |  639 |  858 |  588 |  526 |  499 |   584 |   739 |   763 |   741 | down |
|    | 11 | 1182 | 1344 |  926 |  719 |  608 | 13590 | 16251 | 15375 | 14177 | down |
|    | 12 | 1298 | 1613 | 1153 |  988 |  864 |   191 |   194 |   203 |   192 | down |
|    | 17 |  564 |  886 |  561 |  537 |  515 |   147 |   180 |   119 |   128 | down |
|    | 24 | 1201 | 1842 | 1376 | 1042 |  718 |  2050 |  1419 |  1441 |  1363 | down |
|    | 25 | 2023 | 3332 | 2103 | 1956 |  678 |  1848 |  1767 |  1727 |  1699 | down |
|    | 26 | 1573 | 1920 | 1492 | 1237 |  640 |       |       |       |       | down |
|    | 27 | 2713 | 3722 | 2714 | 2141 | 3056 |       |       |       |       | down |
|    | 28 | 1140 | 1536 | 1227 |  800 | 1296 |   891 |  1121 |  1219 |  1160 | down |
|    | 29 |  200 |  213 |  203 |   83 |      |   761 |   769 |   968 |   846 | down |
|    | 36 |  413 |  432 |  434 |  359 |  415 |       |       |       |       | down |
|    | 14 |  217 |  204 |  168 |   89 |  215 |  1366 |  1242 |  1219 |  1060 | down |
|    | 30 |17617 |25783 |21298 |17727 |21489 |       |       |       |       | down |
|    | 19 |10397 |19133 |14127 |11409 |18228 | 24398 | 24972 | 24312 | 22036 | down |
|    | 15 | 1973 | 1950 | 1589 | 1273 |  901 |   379 |   384 |   405 |   403 | down |
|    | 37 |  239 |  248 |  257 |  200 |  165 |   200 |   179 |   202 |   190 | down |

Example 2

This example demonstrates that mir-181s are associated with HSC-HCC and contribute to the function of liver cancer stem cells.

The expression levels of mir-181s in both precursors (A) and mature miRNAs (B) are significantly increased in HSC-HCCs and BDE-HCCs but decreased in HP- and MH-HCCs, versus their corresponding non-HCC tissues. HSC-HCC and BDE-HCC refer to HCCs with stem cell-like features and bile duct epithelium-like features, respectively. Mir-181 expression, based on miRNA microarray analysis of miRNA precursors in each HCC subtype versus corresponding non-HCC tissues from 230 patients is shown in FIG. 1A-E for mir-181a1, mir-181a2, mir-181b1, mir-181b2 and mir-181c, respectively. Gene expression ratios are shown (mean±95% CI) in log 2 scale. FIGS. 1F-J shows RT-PCR analysis of all mature mir-181s in 40 HCC and non-HCC sample pairs. Scatter plot analysis of pre-mir-181s and mature mir-181s is shown in FIG. 2, with r-values representing Spearman's correlation coefficient.

Figure 9:
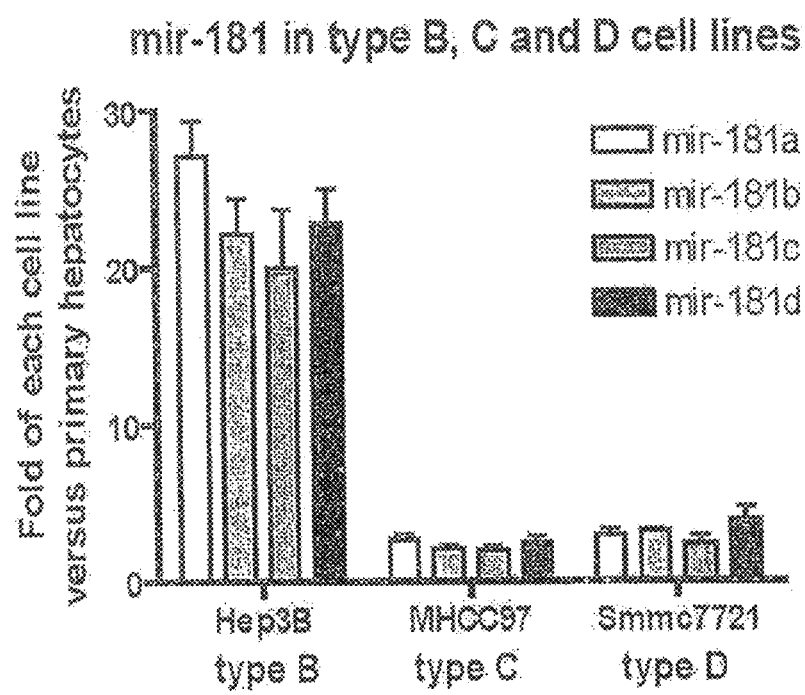
FIG. 9 is a graph of the fold of mir-181a, mir-181b, mir-181c, and mir-181d in each cell line (Hep3b type B (HSC-HCC), MHCC97 type C (HP-HCC), 5 mmc7721 type D (MH-HCC)) versus primary hepatocytes.

Next, mir-181 expression was positively correlated with Wnt-β-catenin signaling activation and negatively correlated with many mature hepatocyte genes in both clinical specimens and cultured HCC cell lines. Hierarchical clustering was conducted of 5 pre-mir-181s, 15 hepatocyte-specific genes, and 5 beta-catenin associated genes whose expression was significantly correlated with each other (p<0.001) from correlation analysis between microarray data and mRNA array data. In 3 different types of HCC cell lines, mir-181 expression was positively correlated with beta-catenin protein level (FIG. 9).

After culturing HuH1 cells with ESC culture media, which is a basal medium optimized for growth of undifferentiated embryonic stem (ES) cells, the expression of mir-181 and beta-catenin regulated genes was increased and the expression of hepatocyte-specific genes was decreased as analyzed by qRT-PCR (FIGS. 3A-C) as well as immunoblotting using antibodies to beta-catenin and actin (as a control). Following withdrawal of ESC media, the expression of the above genes was changed reversely, as analyzed by qRT-PCR (FIGS. 3D-F). Gene expression was measured in triplicate and is shown as mean±SD.

Example 3

This example demonstrates that mir-181 expression is involved in the activation of wnt-beta-catenin signaling.

Figure 4:
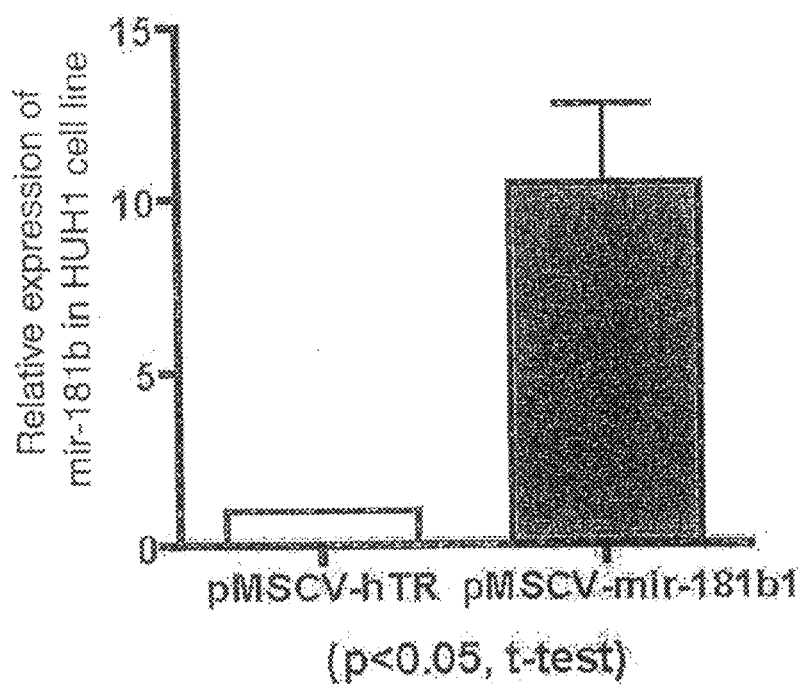
FIG. 4 is a graph of the relative expression of mir-181b in pMSCV-hTR and pMSCV-mir-181b1 treated HuH1 cells.

After transfecting pMSCV-mir-181b-1 to HuH1 cells, mir-181b was detected by RT-PCR and expression was compared to that of pMSCV-hTR cells. Gene expression was measured in triplicate and is shown as mean±SD in FIG. 4. As shown, mir-181 was over expressed in the HuH1 cells.

Figure 5:
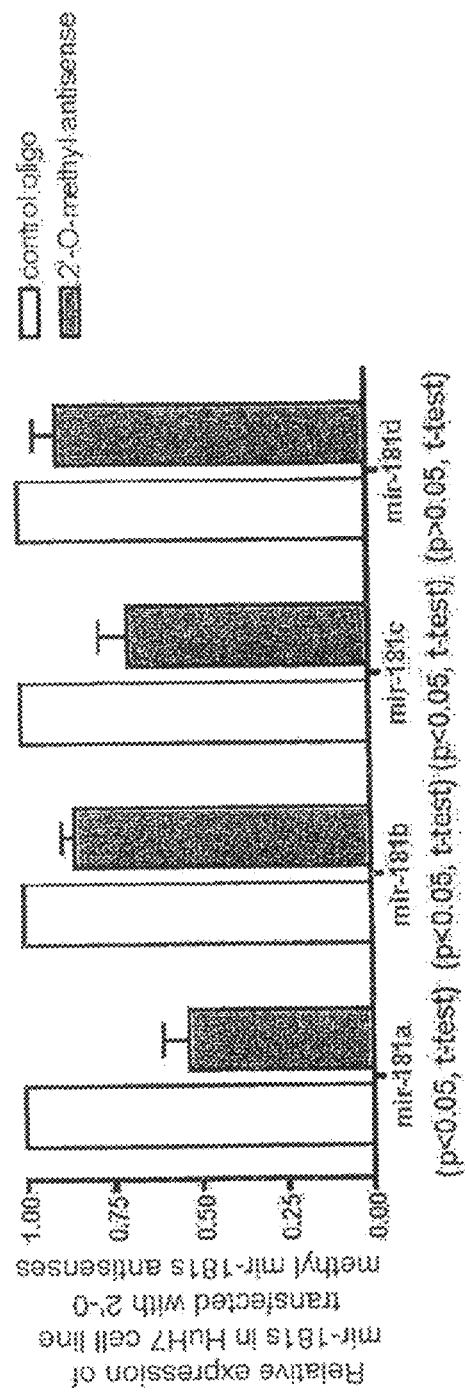
FIG. 5 is a graph of the relative expression of mir-181s in HuH7 cells transfected with 2'-O-methyl antisense versus control.

HuH7 cells were treated with 2'-O-methyl mir-181s antisense and the expression of all mir-181s was subsequently detected. A significant decrease in gene expression (compared to a control oligo), which was measured in triplicate, is shown as mean±SD in FIG. 5.

Figure 6A:
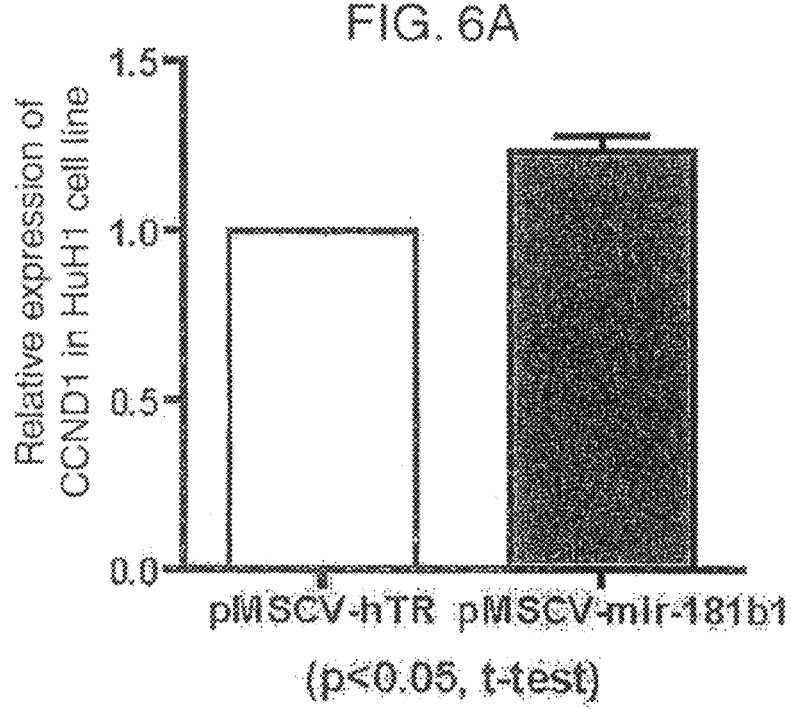
FIG. 6A is a graph of the relative expression of CCND1 in pMSCV-hTR and p-MSCV-mir-181b1 treated HuH1 cells.
Figure 6B:
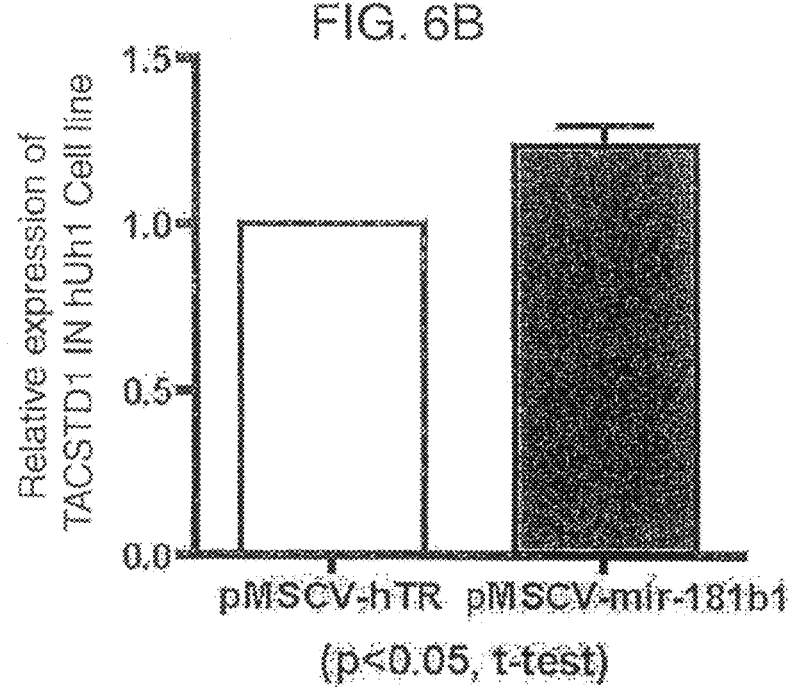
FIG. 6B is a graph of the relative expression of TACTD1 in pMSCV-hTR and p-MSCV-mir-181b1 treated HuH1 cells.
Figure 6C:
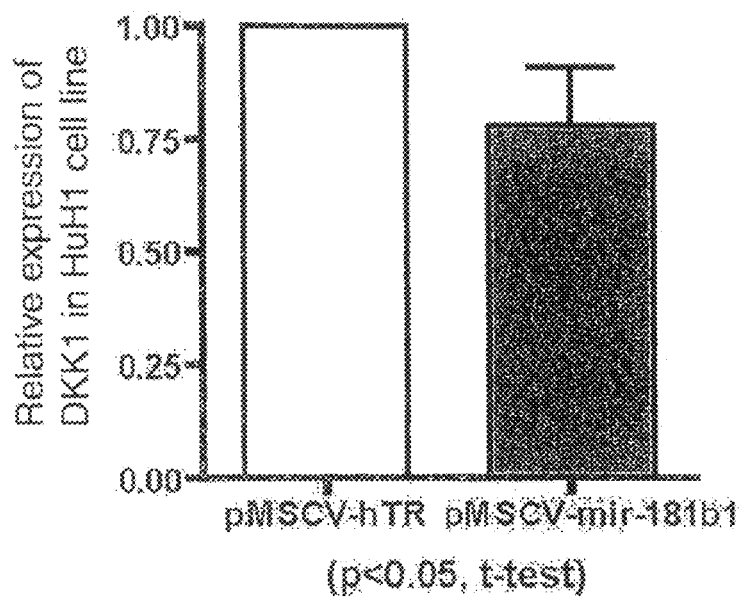
FIG. 6C is a graph of the relative expression of DKK1 in pMSCV-hTR and p-MSCV-mir-181b1 treated HuH1 cells.

Following mir-181 overexpression in Hall cells, the expression of beta-catenin regulated genes (CCND1, TACSTD1, and DKK1) was detected by RT-PCR and compared to expression by pMSCV-hTR cells (FIGS. 6A-C). Cell lysates of cell lines were also analyzed by immunoblots with antibodies to β-catenin and actin.

Figure 6D:
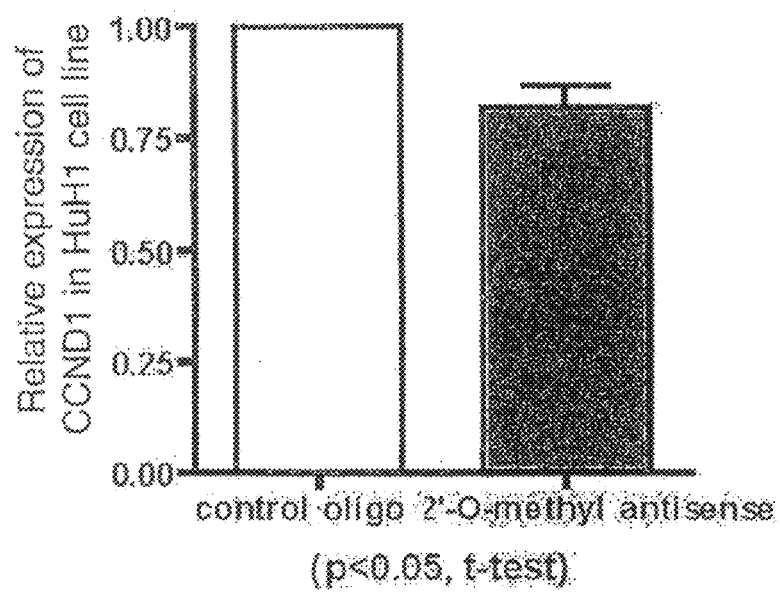
FIG. 6D is a graph of the relative expression of CCND1 in control and antisense treated HuH7 cells.
Figure 6E:
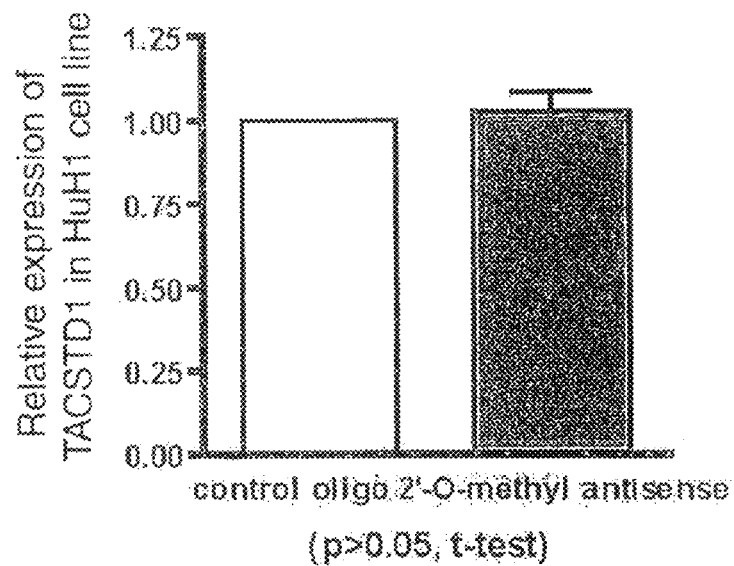
FIG. 6E is a graph of the relative expression of TACSTD1 in control and antisense treated HuH7 cells.
Figure 6F:
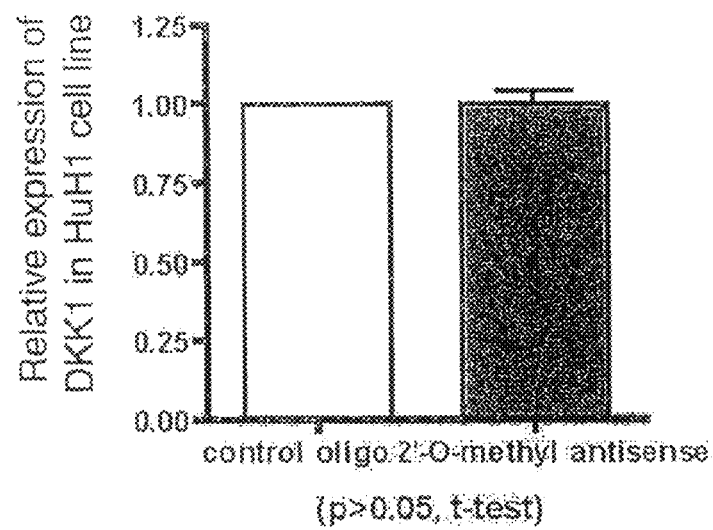
FIG. 6F is a graph of the relative expression of DKK1 in control and antisense treated HuH7 cells.

Following mir-181 downregulation in HuH7 cells, the expression of beta-catenin regulated genes (CCND1, TACSTD1, and DKK1) was detected by RT-PCR and compared to the expression of pMSCV-hTR cells (FIGS. 6D-F). Cell lysates of cell lines were also analyzed by immunoblots with antibodies to B-catenin and actin.

Mir-181s affect wnt-beta-catenin expression. It is possible that this occurs through a functional feedback link. DKK1 is an inhibitor of beta-catenin. Beta-catenin induces mir-181 as well as DKK1, which subsequently inhibits beta-catenin. It is thought that mir-181 acts to inhibit the inhibitory activity of DKK1. Predicted mir-181s binding sites in DKK1 3'-UTR are shown in FIG. 7A-B. The BC001539, *homo sapien* dickkopf homolog 1 cDNA was used. FIG. 7A shows the binding sites in the position of 611-632 of DKK1 3'-UTR. FIG. 7B shows the predicted binding sites in the position of 771-799 of DKK1 3'-UTR.

The predicted transcription factor-4 (TCF-4) binding sites ((A/T)(A/T)CAAAG) OR (CTTTG(A/T)(A/T)) in mir-181s' promoters are shown in FIGS. 8A-D. 6,060 base pairs were analyzed at the upstream of transcriptional start site. FIG. 8A shows the promoter of mir-181a1 and mir-181b1 in Chromosome 1, for which the NW_926128, *homo sapiens* chromosome 1 genomic contig was used. FIG. 8B shows the promoter of mir-181a2 and mir-181b2 in Chromosome 9, for which the NT_008470 homo sapien chromosome 9 genomic contig was used. In the Sanger Database, both EST genes are predicted in the region of mir-181c and mir-181d locating, which have different transcriptional start sites (FIGS. 8C-D). The promoter of mir-181c and mir-181d in Chromosome 19 in FIG. 8C is the promoter from ENSESTT00000290819. The promoter of mir-181c and mir-181d in Chromosome 19 in FIG. 8D is the promoter from ENSESTT00000290818.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of determining a hepatocellular carcinoma (HCC) subtype in a subject comprising
   a) obtaining a sample from the subject,
   b) analyzing the sample, by laboratory assay, for a change in the level of expression of one or more biomarkers relative to the level of expression of a corresponding biomarker in at least one control sample, wherein the biomarker consists of at least one of the biomarkers identified by miR-221 and miR-222, and
   c) correlating the change in the level of expression of the biomarkers, relative to the level of expression of the corresponding biomarker in the control sample, with the presence of bile duct epithelium-like hepatocellular carcinoma (BDE-HCC) subtype of HCC in the subject,
   d) determining a hepatocellular carcinoma (HCC) subtype as bile duct epithelium-like hepatocellular carcinoma (BDE-HCC) subtype if biomarkers for at least one of miR-221 and miR-222 in the sample are high relative to the level of expression of the corresponding biomarker in normal liver as the at least one control sample, and determining a hepatocellular carcinoma (HCC) subtype as not BDE-HCC subtype if biomarkers for at least one of miR-221 and miR-222 in the sample are not high relative to the level of expression of the corresponding biomarker in normal liver as the at least one control sample.

2. The method of claim 1, wherein the sample is selected from the group consisting of liver tumor tissue, liver normal tissue, frozen biopsy tissue, paraffin-embedded biopsy tissue, serum, plasma, and combinations thereof.

3. The method of claim 1, wherein the sample is analyzed by one or more methods selected from the group consisting of micro array techniques, PCR amplification, RNA hybridization, in situ hybridization, gel electrophoresis, and combinations thereof.

4. The method of claim 1, further including a step (e) of: further discriminating bile duct epithelial (BDE-HCC) subtype from hepatic stem cell (HSC-HCC) subtype and hepatocytic progenitor subtype (HP-HCC) by correlating an alteration in the level of expression of one or more of the biomarkers, relative to the level of expression of the corresponding biomarker in the control sample.

5. The method of claim 1, wherein step (b) further comprises determining an increased level of expression of at least both of miR-221 and miR-222 biomarkers.

6. The method of claim 1, wherein step (b) further includes analyzing the sample for a change in the level of expression of at least one or more additional biomarkers identified by miR-106a, miR-106b, and miR-17, and
   wherein step (c) further includes correlating an increase in the level of expression of at least one or more additional biomarkers identified by miR-106a, miR-106b, and miR-17, relative to the level of expression of the corresponding additional biomarker in normal liver as the at least one control sample, with the presence of BDE-HCC subtype in the subject.

7. The method of claim 1, wherein step (b) further includes analyzing the sample for a change in the level of expression of at least one or more additional biomarkers identified by miR-25, miR-32, miR-92-1, miR-122a, miR-125b-1, and miR-125b-2, and
   wherein step (c) further includes correlating a decrease in the level of expression of at least one or more additional biomarkers identified by miR-25, miR-32, miR-92-1, miR-122a, miR-125b-1, and miR-125b-2, relative to the level of expression of the corresponding additional biomarker in normal liver as the at least one control sample, with the presence of BDE-HCC subtype in the subject.

8. The method of claim 1, wherein step (b) further includes analyzing the sample for a change in the level of expression of at least one or more additional biomarkers identified by miR-106a, miR-17, miR-32, miR-92-1, miR-122a, miR-125b-1, and miR-125b-2, and
   wherein step (c) further includes correlating a decrease in the level of expression of at least one or more additional biomarkers identified by miR-106a, miR-17, miR-32, miR-92-1, miR-122a, miR-125b-1, and miR-125b-2, relative to the level of expression of the corresponding additional biomarker in bile duct epithelium-like non-hepatocellular carcinoma (BDE-non-HCC) as the at least one control sample, with the presence of BDE-HCC subtype in the subject.

\* \* \* \* \*

UNITED STATES PATENT AND TRADEMARK OFFICE
CERTIFICATE OF CORRECTION

PATENT NO. : 8,465,917 B2
APPLICATION NO. : 12/663586
DATED : June 18, 2013
INVENTOR(S) : Xin Wei Wang et al.

Page 1 of 2

It is certified that error appears in the above-identified patent and that said Letters Patent is hereby corrected as shown below:

In the Claims

Column 35, claim 1, line 33, after "miR-221" insert -- [SEQ ID NO: 25] --.

Column 35, claim 1, line 33, after "miR-222" insert -- [SEQ ID NO: 26] --.

Column 36, claim 6, line 30, after "miR-106a" insert -- [SEQ ID NO: 20] --.

Column 36, claim 6, line 30, after "miR-106b" insert -- [SEQ ID NO: 21] --.

Column 36, claim 6, line 30, after "miR-17" insert -- [SEQ ID NO: 16] --.

Column 36, claim 6, line 33, after "miR-106a" insert -- [SEQ ID NO: 20] --.

Column 36, claim 6, line 33, after "miR-106b" insert -- [SEQ ID NO: 21] --.

Column 36, claim 6, line 34, after "miR-17" insert -- [SEQ ID NO: 16] --.

Column 36, claim 7, line 41, after "miR-25" insert -- [SEQ ID NO: 27] --.

Column 36, claim 7, line 41, after "miR-32" insert -- [SEQ ID NO: 28] --.

Column 36, claim 7, line 41, after "miR-92-1" insert -- [SEQ ID NO: 30] --.

Column 36, claim 7, line 41, after "miR-122a" insert -- [SEQ ID NO: 31] --.

Column 36, claim 7, line 41, after "miR-125b-1" insert -- [SEQ ID NO: 32] --.

Column 36, claim 7, line 42, after "miR-125b-2" insert -- [SEQ ID NO: 33] --.

Column 36, claim 7, line 45, after "miR-25" insert -- [SEQ ID NO: 27] --.

Column 36, claim 7, line 45, after "miR-32" insert -- [SEQ ID NO: 28] --.

Signed and Sealed this
Thirtieth Day of July, 2013

Teresa Stanek Rea
*Acting Director of the United States Patent and Trademark Office*

CERTIFICATE OF CORRECTION (continued)
U.S. Pat. No. 8,465,917 B2

Column 36, claim 7, line 45, after "miR-92-1" insert -- [SEQ ID NO: 30] --.

Column 36, claim 7, line 46, after "miR-122a" insert -- [SEQ ID NO: 31] --.

Column 36, claim 7, line 46, after "miR-125b-1" insert -- [SEQ ID NO: 32] --.

Column 36, claim 7, line 46, after "miR-125b-2" insert -- [SEQ ID NO: 33] --.

Column 36, claim 8, line 54, after "miR-106a" insert -- [SEQ ID NO: 20] --.

Column 36, claim 8, line 54, after "miR-17" insert -- [SEQ ID NO: 16] --.

Column 36, claim 8, line 54, after "miR-32" insert -- [SEQ ID NO: 28] --.

Column 36, claim 8, line 54, after "miR-92-1" insert -- [SEQ ID NO: 30] --.

Column 36, claim 8, line 54, after "miR-122a" insert -- [SEQ ID NO: 31] --.

Column 36, claim 8, line 54, after "miR-125b-1" insert -- [SEQ ID NO: 32] --.

Column 36, claim 8, line 55, after "miR-125b-2" insert -- [SEQ ID NO: 33] --.

Column 36, claim 8, line 58, after "miR-106a" insert -- [SEQ ID NO: 20] --.

Column 36, claim 8, line 58, after "miR-17" insert -- [SEQ ID NO: 16] --.

Column 36, claim 8, line 58, after "miR-32" insert -- [SEQ ID NO: 28] --.

Column 36, claim 8, line 59, after "miR-92-1" insert -- [SEQ ID NO: 30] --.

Column 36, claim 8, line 59, after "miR-122a" insert -- [SEQ ID NO: 31] --.

Column 36, claim 8, line 59, after "miR-125b-1" insert -- [SEQ ID NO: 32] --.

Column 36, claim 8, line 59, after "miR-125b-2" insert -- [SEQ ID NO: 33] --.

SEQUENCE LISTING

<160> NUMBER OF SEQ ID NOS: 45

<210> SEQ ID NO 1
<211> LENGTH: 21
<212> TYPE: RNA
<213> ORGANISM: Homo sapiens

<400> SEQUENCE: 1
ugagguagua gguuguauag u                                              21

<210> SEQ ID NO 2
<211> LENGTH: 22
<212> TYPE: RNA
<213> ORGANISM: Homo sapiens

<400> SEQUENCE: 2
ugagguagua gguuguauag uu                                             22

<210> SEQ ID NO 3
<211> LENGTH: 22
<212> TYPE: RNA
<213> ORGANISM: Homo sapiens

```
<400> SEQUENCE: 3
ugagguagua gguuguaugg uu                                         22

<210> SEQ ID NO 4
<211> LENGTH: 22
<212> TYPE: RNA
<213> ORGANISM: Homo sapiens

<400> SEQUENCE: 4
ugagguagua gguugugugg uu                                         22

<210> SEQ ID NO 5
<211> LENGTH: 22
<212> TYPE: RNA
<213> ORGANISM: Homo sapiens

<400> SEQUENCE: 5
ugagguagua gguuguaugg uu                                         22

<210> SEQ ID NO 6
<211> LENGTH: 21
<212> TYPE: RNA
<213> ORGANISM: Homo sapiens

<400> SEQUENCE: 6
agagguagua gguugcauag u                                          21

<210> SEQ ID NO 7
<211> LENGTH: 21
<212> TYPE: RNA
<213> ORGANISM: Homo sapiens

<400> SEQUENCE: 7
ugagguagua gauuguauag u                                          21

<210> SEQ ID NO 8
<211> LENGTH: 21
<212> TYPE: RNA
<213> ORGANISM: Homo sapiens

<400> SEQUENCE: 8
ugagguagua guuuguacag u                                          21

<210> SEQ ID NO 9
<211> LENGTH: 22
<212> TYPE: RNA
<213> ORGANISM: Homo sapiens

<400> SEQUENCE: 9
cuuuuugcgg ucugggcuug cu                                         22

<210> SEQ ID NO 10
<211> LENGTH: 22
<212> TYPE: RNA
<213> ORGANISM: Homo sapiens

<400> SEQUENCE: 10
cuuuuugcgg ucugggcuug cu                                         22

<210> SEQ ID NO 11
<211> LENGTH: 22
<212> TYPE: RNA
<213> ORGANISM: Homo sapiens
```

```
<400> SEQUENCE: 11
aacauucauu gcugucggug gg                                              22

<210> SEQ ID NO 12
<211> LENGTH: 22
<212> TYPE: RNA
<213> ORGANISM: Homo sapiens

<400> SEQUENCE: 12
aacauucauu gcugucggug gg                                              22

<210> SEQ ID NO 13
<211> LENGTH: 21
<212> TYPE: RNA
<213> ORGANISM: Homo sapiens

<400> SEQUENCE: 13
uagguaguuu cauguuguug g                                               21

<210> SEQ ID NO 14
<211> LENGTH: 23
<212> TYPE: RNA
<213> ORGANISM: Homo sapiens

<400> SEQUENCE: 14
uccagcuccu auaugaugcc uuu                                             23

<210> SEQ ID NO 15
<211> LENGTH: 22
<212> TYPE: RNA
<213> ORGANISM: Homo sapiens

<400> SEQUENCE: 15
aaagugcugu ucgugcaggu ag                                              22

<210> SEQ ID NO 16
<211> LENGTH: 24
<212> TYPE: RNA
<213> ORGANISM: Homo sapiens

<400> SEQUENCE: 16
caaagugcuu acagugcagg uagu                                            24

<210> SEQ ID NO 17
<211> LENGTH: 22
<212> TYPE: RNA
<213> ORGANISM: Homo sapiens

<400> SEQUENCE: 17
aacauucaac cugucgguga gu                                              22

<210> SEQ ID NO 18
<211> LENGTH: 23
<212> TYPE: RNA
<213> ORGANISM: Homo sapiens

<400> SEQUENCE: 18
cagugcaaua guauugucaa agc                                             23

<210> SEQ ID NO 19
<211> LENGTH: 21
<212> TYPE: RNA
<213> ORGANISM: Homo sapiens
```

```
<400> SEQUENCE: 19
uauugcacuu gucccggccu g                                              21

<210> SEQ ID NO 20
<211> LENGTH: 24
<212> TYPE: RNA
<213> ORGANISM: Homo sapiens

<400> SEQUENCE: 20
aaaagugcuu acagugcagg uagc                                           24

<210> SEQ ID NO 21
<211> LENGTH: 21
<212> TYPE: RNA
<213> ORGANISM: Homo sapiens

<400> SEQUENCE: 21
uaaagugcug acagugcaga u                                              21

<210> SEQ ID NO 22
<211> LENGTH: 23
<212> TYPE: RNA
<213> ORGANISM: Homo sapiens

<400> SEQUENCE: 22
aacauucaac gcugucggug agu                                            23

<210> SEQ ID NO 23
<211> LENGTH: 23
<212> TYPE: RNA
<213> ORGANISM: Homo sapiens

<400> SEQUENCE: 23
aacauucaac gcugucggug agu                                            23

<210> SEQ ID NO 24
<211> LENGTH: 23
<212> TYPE: RNA
<213> ORGANISM: Homo sapiens

<400> SEQUENCE: 24
uaaagugcuu auagugcagg uag                                            23

<210> SEQ ID NO 25
<211> LENGTH: 22
<212> TYPE: RNA
<213> ORGANISM: Homo sapiens

<400> SEQUENCE: 25
agcuacauug ucugcugggu uu                                             22

<210> SEQ ID NO 26
<211> LENGTH: 24
<212> TYPE: RNA
<213> ORGANISM: Homo sapiens

<400> SEQUENCE: 26
agcuacaucu ggcuacuggg ucuc                                           24

<210> SEQ ID NO 27
<211> LENGTH: 22
<212> TYPE: RNA
<213> ORGANISM: Homo sapiens
```

```
<400> SEQUENCE: 27
cauugcacuu gucucggucu ga                                              22

<210> SEQ ID NO 28
<211> LENGTH: 21
<212> TYPE: RNA
<213> ORGANISM: Homo sapiens

<400> SEQUENCE: 28
uauugcacau uacuaaguug c                                               21

<210> SEQ ID NO 29
<211> LENGTH: 22
<212> TYPE: RNA
<213> ORGANISM: Homo sapiens

<400> SEQUENCE: 29
gcacauuaca cggucgaccu cu                                              22

<210> SEQ ID NO 30
<211> LENGTH: 21
<212> TYPE: RNA
<213> ORGANISM: Homo sapiens

<400> SEQUENCE: 30
uauugcacuu gucccggccu g                                               21

<210> SEQ ID NO 31
<211> LENGTH: 23
<212> TYPE: RNA
<213> ORGANISM: Homo sapiens

<400> SEQUENCE: 31
uggaguguga caaugguguu ugu                                             23

<210> SEQ ID NO 32
<211> LENGTH: 22
<212> TYPE: RNA
<213> ORGANISM: Homo sapiens

<400> SEQUENCE: 32
ucccugagac ccuaacuugu ga                                              22

<210> SEQ ID NO 33
<211> LENGTH: 22
<212> TYPE: RNA
<213> ORGANISM: Homo sapiens

<400> SEQUENCE: 33
ucccugagac ccuaacuugu ga                                              22

<210> SEQ ID NO 34
<211> LENGTH: 21
<212> TYPE: RNA
<213> ORGANISM: Homo sapiens

<400> SEQUENCE: 34
uagcaccauc ugaaaucggu u                                               21

<210> SEQ ID NO 35
<211> LENGTH: 23
<212> TYPE: RNA
<213> ORGANISM: Homo sapiens
```

```
<400> SEQUENCE: 35
uagcaccauu ugaaaucagu guu                                          23

<210> SEQ ID NO 36
<211> LENGTH: 23
<212> TYPE: RNA
<213> ORGANISM: Homo sapiens

<400> SEQUENCE: 36
cgcaucsccu agggcauugg ugu                                          23

<210> SEQ ID NO 37
<211> LENGTH: 22
<212> TYPE: RNA
<213> ORGANISM: Homo sapiens

<400> SEQUENCE: 37
cacccguaga accgaccuug cg                                           22

<210> SEQ ID NO 38
<211> LENGTH: 23
<212> TYPE: RNA
<213> ORGANISM: Homo sapiens

<400> SEQUENCE: 38
uagcaccauu ugaaaucagu guu                                          23

<210> SEQ ID NO 39
<211> LENGTH: 20
<212> TYPE: RNA
<213> ORGANISM: Homo sapiens

<400> SEQUENCE: 39
uagcaccauu ugaaaucggu                                              20

<210> SEQ ID NO 40
<211> LENGTH: 22
<212> TYPE: RNA
<213> ORGANISM: Homo sapiens

<400> SEQUENCE: 40
aaugaucaua gcaccuugga ug                                           22

<210> SEQ ID NO 41
<211> LENGTH: 23
<212> TYPE: RNA
<213> ORGANISM: Homo sapiens

<400> SEQUENCE: 41
ugaguggcug ucgcaacuua caa                                          23

<210> SEQ ID NO 42
<211> LENGTH: 22
<212> TYPE: RNA
<213> ORGANISM: Homo sapiens

<400> SEQUENCE: 42
ggguggcugu cguuacuuac aa                                           22

<210> SEQ ID NO 43
<211> LENGTH: 22
<212> TYPE: RNA
<213> ORGANISM: Homo sapiens
```

```
<400> SEQUENCE: 43
ugaguggcug uccaacuuac aa                                           22

<210> SEQ ID NO 44
<211> LENGTH: 24
<212> TYPE: RNA
<213> ORGANISM: Homo sapiens

<400> SEQUENCE: 44
uuggguggcu guuguuacuu acaa                                         24

<210> SEQ ID NO 45
<211> LENGTH: 29
<212> TYPE: RNA
<213> ORGANISM: Homo sapiens

<400> SEQUENCE: 45 aacguccu gaaagaaggu caagugugu                                      29
```